(12) United States Patent
Alphonse

(10) Patent No.: US 7,184,148 B2
(45) Date of Patent: Feb. 27, 2007

(54) LOW COHERENCE INTERFEROMETRY UTILIZING PHASE

(75) Inventor: Gerard A. Alphonse, Princeton, NJ (US)

(73) Assignee: Medeikon Corporation, Ewing, NJ (US)

( * ) Notice: Subject to any disclaimer, the term of this patent is extended or adjusted under 35 U.S.C. 154(b) by 278 days.

(21) Appl. No.: 10/845,849

(22) Filed: May 14, 2004

(65) Prior Publication Data

US 2005/0254057 A1 Nov. 17, 2005

(51) Int. Cl.
*G01B 9/02* (2006.01)

(52) U.S. Cl. ...................................... 356/479

(58) Field of Classification Search ................ 356/477, 356/479, 481, 517; 250/227.19, 227.27; 600/476

See application file for complete search history.

(56) References Cited

U.S. PATENT DOCUMENTS

| | | | |
|---|---|---|---|
| 4,883,953 A | 11/1989 | Koashi |
| 5,202,745 A | 4/1993 | Sorin |
| 5,321,501 A | 6/1994 | Swanson |
| 5,341,205 A | 8/1994 | McLandrich |
| 5,383,467 A | 1/1995 | Auer |
| 5,398,681 A | 3/1995 | Kupershmidt |

(Continued)

FOREIGN PATENT DOCUMENTS

| | | |
|---|---|---|
| EP | 0831312 A1 | 3/1998 |
| EP | 0831312 B1 | 10/2001 |

(Continued)

OTHER PUBLICATIONS

PCT International Search Report, PCT/US2005/015373, Apr. 5, 2005.

(Continued)

*Primary Examiner*—Gregory J. Toatley, Jr.
*Assistant Examiner*—Michael A. Lyons
(74) *Attorney, Agent, or Firm*—Cantor Colburn LLP

(57) ABSTRACT

A method for determining a characteristic of an analyte in a biological sample, the method comprising: directing broadband light by means of a sensing light path at the biological sample, at a target depth defined by the sensing light path and a reference light path; and receiving the broadband light reflected from the biological sample by means of the sensing light path. The method also includes: directing the broadband light by means of the reference light path at a reflecting device; receiving the broadband light reflected from the reflecting device by means of the reference light path; and interfering the broadband light reflected from the biological sample and the broadband light reflected from the reflecting device. The method further includes: detecting the broadband light resulting from interference of the broadband light reflected from the biological sample and the broadband light reflected from the reflecting device; and modulating an effective light path length of at least one of the reference light path and the sensing light path to enhance interference of the broadband light reflected from the biological sample and the broadband light reflected from the reflecting device. The method continues with: determining a magnitude of change of the effective light path length introduced by the modulating when interference is enhanced; determining a variation in an index of refraction from a ratio of the magnitude of change of the effective light path length and the target depth; and determining the characteristic of the analyte in the biological sample from the variation in the index of refraction.

25 Claims, 18 Drawing Sheets

U.S. PATENT DOCUMENTS

| | | |
|---|---|---|
| 5,434,791 A | 7/1995 | Koko |
| 5,459,570 A | 10/1995 | Swanson |
| 5,465,147 A | 11/1995 | Swanson |
| 5,491,552 A | 2/1996 | Knuttel |
| 5,501,226 A | 3/1996 | Petersen |
| 5,507,288 A | 4/1996 | Bocker |
| 5,549,114 A | 8/1996 | Petersen |
| 5,565,986 A | 10/1996 | Knuttel |
| 5,582,171 A | 12/1996 | Chornenky |
| 5,710,630 A | 1/1998 | Essenpreis |
| 5,830,145 A | 11/1998 | Tenhoff |
| 5,835,215 A | 11/1998 | Toida et al. |
| 5,835,642 A | 11/1998 | Gelikonov |
| 5,836,877 A | 11/1998 | Zavislan |
| 5,847,827 A | 12/1998 | Fercher |
| 5,867,268 A | 2/1999 | Gelikonov |
| 5,877,856 A | 3/1999 | Fercher |
| 5,883,717 A | 3/1999 | DiMarzio |
| 5,892,583 A | 4/1999 | Li |
| 5,905,572 A | 5/1999 | Li |
| 5,920,390 A | 7/1999 | Farahi |
| 5,921,926 A | 7/1999 | Rolland |
| 5,943,133 A | 8/1999 | Zeylikovich |
| 5,956,355 A | 9/1999 | Swanson |
| 5,962,852 A | 10/1999 | Knuettel |
| 5,991,697 A | 11/1999 | Nelson |
| 5,994,690 A | 11/1999 | Kulkarni |
| 6,002,480 A | 12/1999 | Izatt |
| 6,006,128 A | 12/1999 | Izatt |
| 6,014,214 A | 1/2000 | Li |
| 6,020,963 A | 2/2000 | DiMarzio |
| 6,037,579 A | 3/2000 | Chan |
| 6,053,613 A | 4/2000 | Wei |
| 6,057,920 A | 5/2000 | Fercher |
| 6,069,698 A | 5/2000 | Ozawa |
| 6,072,765 A | 6/2000 | Rolland |
| 6,111,645 A | 8/2000 | Tearney |
| 6,124,930 A | 9/2000 | Fercher |
| 6,134,003 A | 10/2000 | Tearney |
| 6,141,577 A | 10/2000 | Rolland |
| 6,144,449 A | 11/2000 | Knuettel |
| 6,152,875 A | 11/2000 | Hakamata |
| 6,160,826 A | 12/2000 | Swanson et al. |
| 6,175,669 B1 | 1/2001 | Colston et al. |
| 6,191,862 B1 | 2/2001 | Swanson et al. |
| 6,198,540 B1 | 3/2001 | Ueda et al. |
| 6,201,608 B1 | 3/2001 | Mandella et al. |
| 6,208,415 B1 | 3/2001 | De Boer et al. |
| 6,219,055 B1 | 4/2001 | Bhargava |
| 6,226,089 B1 | 5/2001 | Hakamata |
| 6,233,055 B1 | 5/2001 | Mandella et al. |
| 6,252,666 B1 | 6/2001 | Mandella et al. |
| 6,268,921 B1 | 7/2001 | Seitz et al. |
| 6,282,011 B1 | 8/2001 | Tearney et al. |
| 6,288,784 B1 | 9/2001 | Hitzenberger et al. |
| 6,304,373 B1 | 10/2001 | Zavislan |
| 6,307,633 B1 | 10/2001 | Mandella et al. |
| 6,307,634 B2 | 10/2001 | Hitzenberger et al. |
| 6,330,063 B1 | 12/2001 | Knuettel et al. |
| 6,351,325 B1 | 2/2002 | Mandella et al. |
| 6,370,422 B1 | 4/2002 | Richards-Kortum |
| 6,377,349 B1 | 4/2002 | Fercher |
| 6,381,015 B1 | 4/2002 | Sonehara et al. |
| 6,381,025 B1 | 4/2002 | Bornhop |
| 6,381,490 B1 | 4/2002 | Ostrovsky |
| 6,384,915 B1 | 5/2002 | Everett et al. |
| 6,385,358 B1 | 5/2002 | Everett et al. |
| 6,390,978 B1 | 5/2002 | Irion et al. |
| 6,407,872 B1 | 6/2002 | Lai et al. |
| 6,419,360 B1 | 7/2002 | Hauger et al. |
| 6,421,164 B2 | 7/2002 | Tearney et al. |
| 6,423,956 B1 | 7/2002 | Mandella et al. |
| 6,430,455 B1 | 8/2002 | Rebello |
| 6,437,867 B2 | 8/2002 | Zeylikovich et al. |
| 6,441,356 B1 | 8/2002 | Mandella et al. |
| 6,445,939 B1 | 9/2002 | Swanson et al. |
| 6,445,944 B1 | 9/2002 | Ostrovsky |
| 6,456,769 B1 | 9/2002 | Furusawa et al. |
| 6,466,713 B2 | 10/2002 | Everett et al. |
| 6,469,489 B1 | 10/2002 | Bourquin et al. |
| 6,477,403 B1 | 11/2002 | Eguchi et al. |
| 6,485,413 B1 | 11/2002 | Boppart et al. |
| 6,496,267 B1 | 12/2002 | Takaoka |
| 6,498,948 B1 | 12/2002 | Ozawa et al. |
| 6,501,551 B1 | 12/2002 | Tearney et al. |
| 6,507,747 B1 | 1/2003 | Gowda et al. |
| 6,519,076 B2 | 2/2003 | Fisher et al. |
| 6,522,913 B2 | 2/2003 | Panescu et al. |
| 6,525,862 B2 | 2/2003 | Fisher et al. |
| 6,527,708 B1 | 3/2003 | Nakamura et al. |
| 6,538,817 B1 | 3/2003 | Farmer et al. |
| 6,546,272 B1 | 4/2003 | MacKinnon et al. |
| 6,549,801 B1 | 4/2003 | Chen et al. |
| 6,552,796 B2 | 4/2003 | Magnin et al. |
| 6,564,087 B1 | 5/2003 | Pitris et al. |
| 6,564,089 B2 | 5/2003 | Izatt et al. |
| 6,570,659 B2 | 5/2003 | Schmitt |
| 6,571,117 B1 | 5/2003 | Marbach |
| 6,577,394 B1 | 6/2003 | Zavislan |
| 6,615,071 B1 | 9/2003 | Casscells, III |
| 2001/0047137 A1 | 11/2001 | Moreno |
| 2003/0023152 A1 | 1/2003 | Abbink |
| 2003/0023170 A1 | 1/2003 | Gardner et al. |
| 2003/0028100 A1 | 2/2003 | Tearney |
| 2003/0055307 A1 | 3/2003 | Elmaleh |
| 2003/0076508 A1 | 4/2003 | Cornsweet |
| 2003/0137669 A1 | 7/2003 | Rollins |
| 2003/0171691 A1 | 9/2003 | Casscella |

FOREIGN PATENT DOCUMENTS

| | | |
|---|---|---|
| WO | WO 92/19930 | 4/1992 |
| WO | WO 97/32182 | 9/1997 |
| WO | WO9932897 A2 | 12/1997 |
| WO | WO9957507 A1 | 4/1998 |
| WO | WO01120602 A2 | 8/2000 |
| WO | WO2002080767 A1 | 3/2002 |
| WO | WO2003010510 A2 | 7/2002 |
| WO | WO2003088817 A2 | 10/2003 |

OTHER PUBLICATIONS

PCT International Search Report, PCT/US2005/015558, Apr. 5, 2005.

PCT International Search Report, PCT/US2005/015372, Apr. 5, 2005.

Optical Coherence tomography—principles and applications, by A.F. Fercher, W. Drexler, C.K. Hitzenberger and T. Lasser, Institute of Physics Publishing, Reports on Progress in Physics, Jan. 20, 2003, pp. 239-303.

Low Coherence Interferometric Fibre Multiplexed Sensor Systems Using an Integrated-Optical Configuration, by A.J. Rogers, M.J. Plissi, Department of Electronic and Electrical Engineering, King's College London, UK Spie vol. 2510 XP-002112588.

Integrated Optic Error Detecting Circuit Using Ti:Linbo3 Interferometric Light Modulaters by Hiroshi Haga, Masato Ohta, Masayuki Izutsu and Tadasi Sueta. Faculty of Engineering Science, Osaka University Toyonaka, Osaka 560, Japan IOOOC-ECOC '85.

Recent progress in fibre optic low-coherence interferometry by Yun-Jiang Rao and David A. Jackson Applied Optics Group, Physics Dept., University of Kent at Canterbury, Kent CT2 7NR, UK Meas. Sci. Technol. 7 (1996) pp. 981-999.

Joseph M. Schmitt, "Optical Coherence Tomography (OCT): A Review," *IEEE J. Select Topics in Quant.* Elect. vol. 5., No. 4, Jul/Aug 1999, pp. 1205-1215.

Gerard A. Alphonse, "Design of High-Power Superluminescent Diodes with Low Spectral Modulation," *Proceedings of SPIE*, vol. 4648, pp. 125-138 (2002).

Andrew M. Rollins and Joseph A. Izatt, "Optical Interferometer Designs for Optical Coherence Tomography," *Optics Lett.* vol. 24, No. 21, Nov. 1, 1999, pp. 1484-1486.

Rinat O. Esenaliev, Kirill V. Larin and Irina V. Larina, "Noninvasive Monitoring of Glucose Concentration with Optical Coherence Tomography," *Optics Lett.* vol. 28, No. 13, Jul. 1, 2001, pp. 992-994.

Kirill V. Larin, Moshen S. Eledrisi, Massoud Motemedi, and Rinat O. Esenaliev, "Noninvasive Blood Glucose Monitoring with Optical Coherence Tomography—A Pilot Study in the Human Subjects," *Diabetes Care*, vol. 25, No. 12, Dec. 2002, pp. 2263-2267.

H.C. Casey, Jr. and M.B. Panish, *Heterostructure Lasers Parts A and B*, Academic Press, New York, 1978.

R.W. Waynant, V.M. Chenault, Overview of Non-Invasive Fluid Glucose Measurement Using Optical Techniques to Maintain Glucose Control in Diabetes Mellitus, *LEOS Newsletter*, vol. 12, No. 2, Apr. 1998.

R.J. McNichols, G.L. Cote, Optical Glucose Sensing in Biological Fluids: An Overview, Journal of Biomedical Optics, vol. 5, 2000, pp. 5.

A. Dogariu and G. Popescu, "High-Resolutionspatial and Spectral Characterization of Optical Fields," *Optics & Photonics News*, Dec. 2002, p. 21.

M. Kohl, M. Cope, M. Essenpries, D. Bocker, "Influence of Glucose Concentration on Light Scattering in Tissue-Simulating Phantoms," *Optics Letters*, vol. 19, No. 2, Dec. 15, 1994, pp. 2170.

J. T. Bruulsema, et al, "Correlation Between Blood Glucose Concentration in Diabetics and Noninvasively Measured Tissue Optical Scattering Coefficient," *Optics Letters*, vol. 22, No. 3, Feb. 1, 1997, pp. 190.

C. Lentner, ed. Geigy Scientific Tables, Ciba-Geigy, Basle, Switzerland, 1984, pp. 69.

J.M. Schmidt, S.H. Xiang, K.M.Yung, "Speckle in Optical Coherence Tomography" *J. of Biomedical Optics*, vol. 4, No. 1, Jan. 1999, pp. 95-105.

A. M. Rollins, J.A. Izatt, Optimal Interferometer Designs for Optical Coherence Tomography, *Optics Letters*, vol. 24 (21), Nov. 1, 1999, pp. 1484.

S.L. Jacques, Skin Optics, Oregon Medical Laser Center News, Jan. 1998.

J.M. Schmitt, G. Kumar, Optical Scattering Properties of Soft Tissue: A Discrete Particle Model, *Applied Optics*, vol. 37, No. 13, May $1^{st}$, 1998, pp. 2788.

Aristide Dogariu and Gabriel Popsecu, "Measuring the Phase of Spatially Coherent Polychromatic Fields," School of Optics, University of Central Florida, vol. 89, No. 24, Dec. 9, 2002, pp. 1-2.

John S. Maier et al., "In Vivo Study of Human Tissues with a Portable Near-Infrared Tissue Spectrometer," http://lfd.uiuc.edu/spie95/jm/jmspie95.html, pp. 1-8.

Valery V. Tuchin, "Light Propagation in Tissues with Controlled Optical Properties," *J. Biomedical Optics 2(04)*, 1997, pp. 401-417.

Kirill V. Larin, Massoud Motamedi, Taras V. Ashitkov, and Rinat O. Esenaliev, "Specificity of Noninvasive Blood Glucose Sensing Using Optical Coherence Tomography Technique: A Pilot Study," Physics in Medicine and Biology, Phys. Med. Biol. 48 (2003) pp. 1371-1390.

Akira Ishimaru, "Diffusion of Light in Turbid Material," *Applied Optics*, vol. 28, No. 12, Jun. 15, 1989, pp. 2210-2215.

Sid Bennett and Steven R. Emge, "Fiber Optic Rate Gyro for Land Navigation and Platform Stabilization," Sensors Exp 1994, Cleveland, Ohio, Sep. 20, 1994.

A F. Fercher, K. Mengedoht, and W. Werner, "Eye-Length Measurement By Interferometry with Partially Coherent Light," *Optic Letters*, Optical Society of America, vol. 13 No. 3, Mar. 1988, pp. 186-188.

B.L. Danielson and C.D. Whittenberg, "Guided-wave Reflectometry with Micrometer Resolution," *Applied Optics*, vol. 26, No. 14, Jul. 15, 1987.

Kazumasa Takada, Itaru Yokohama, Kazumori Chida, and Juichi Noda, "New Measurement System for Fault Location in Optical Waveguide Devices Based on an Interferometric Technique," *Applied Optics*, vol. 26, No. 9., May 1, 1987, pp. 1603-1606.

Robert C. Youngquist, Sally Carr and D.E.N. Davies, Optical Coherence-Domain Reflectometry: A New Optical Evaluation Technique, *Optics Letters*, vol. 12, No. 3, Mar. 1987.

Harry Delcher, "Continuous Measurement of Glucose in Interstitial Fluid for Extended Time Periods," SpectRx Inc., pp. 1-8.

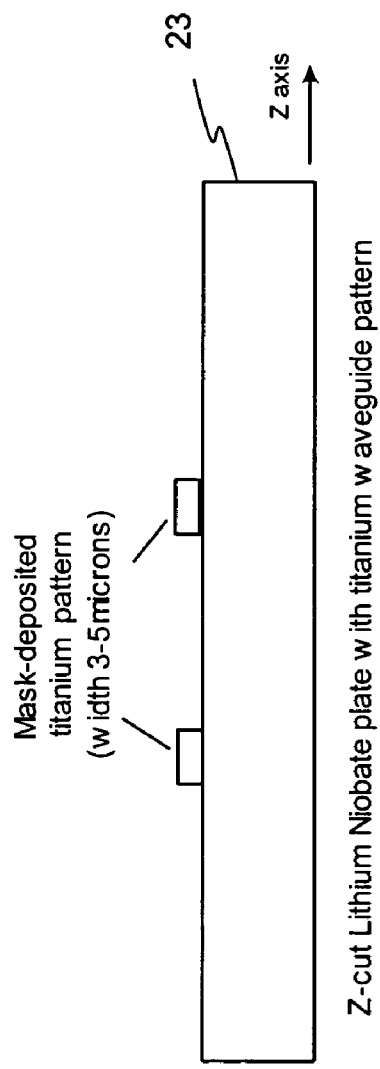
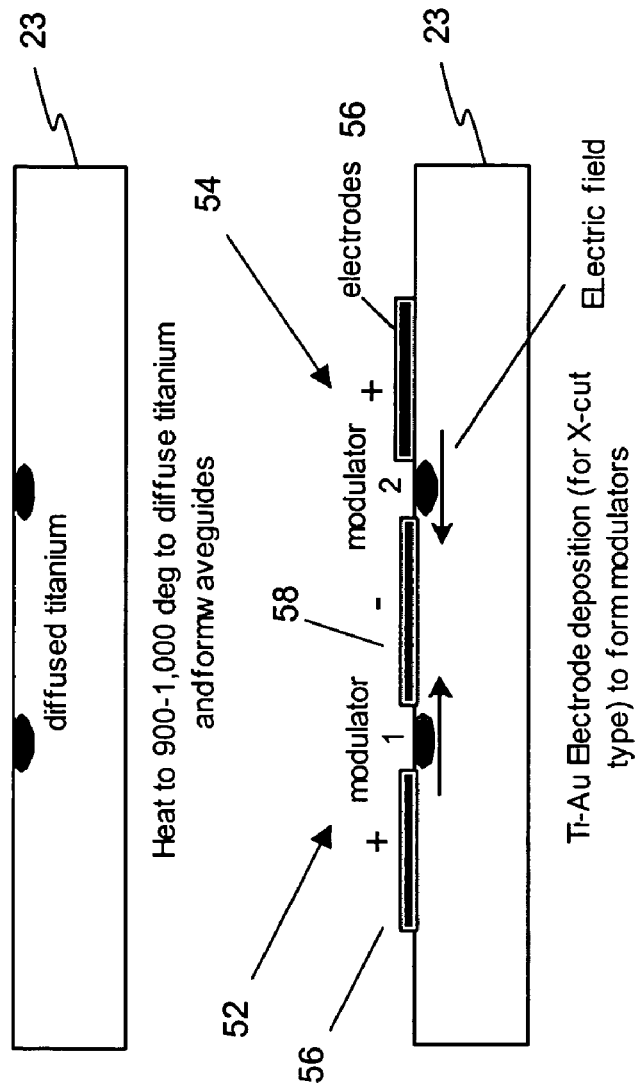

LOW COHERENCE INTERFEROMETRY UTILIZING PHASE

BACKGROUND

The invention concerns a method for low coherence interferometry of a biological sample using phase. The term "biological sample" denotes a body fluid or tissue of an organism. Biological samples are generally optically heterogeneous, that is, they contain a plurality of scattering centers scattering irradiated light. In the case of biological tissue, especially skin tissue, the cell walls and other intra-tissue components form the scattering centers.

Generally, for the qualitative and quantitative analysis in such biological samples, reagents or systems of reagents are used that chemically react with the particular component(s) to be determined. The reaction results in a physically detectable change in the solution of reaction, for instance a change in its color, which can be measured as a measurement quantity. By calibrating with standard samples of known concentration, a correlation is determined between the values of the measurement quantity measured at different concentrations and the particular concentration. These procedures allow accurate and sensitive analyses, but on the other hand they require removing a liquid sample, especially a blood sample, from the body for the analysis ("invasive analysis").

The American Diabetes Association (ADA) estimates that diabetes afflicts nearly 17 million people in the United States. Diabetes can lead to severe complications over time, including heart failure, kidney failure, blindness, and loss of limb due to poor peripheral circulation. According to ADA, complications arising from diabetes cost the U.S. health care system in excess of $132 Billion.

Diabetes complications are largely due to years of poor blood glucose control. The Diabetes Care and Complications Trial (DCCT) carried out by the National Institute of Diabetes and Digestive and Kidney Diseases (NIDDK) demonstrated that more frequent monitoring of blood glucose and insulin levels can prevent many of the long-term complications of diabetes.

Monitoring of blood glucose concentration is key to managing the therapy of diabetes patients. Monitoring results are used to adjust nutrition, medication, and exercise in order to achieve the best possible glucose control, reducing the complications and mortality associated with diabetes. At present, the most widely used method for monitoring of blood glucose by diabetes patients involves chemical analysis of blood samples taken by puncturing the finger or forearm. This method is painful, requires relatively complex operations, is inconvenient due to disruption of daily life, and may become difficult to perform in the long term due to calluses on the fingers and poor circulation. As a result, the average diabetic patient tests his/her blood glucose levels less than twice a day versus the recommended four or more times per day. Non-invasive blood glucose monitoring techniques with accuracies equal to or better than the current chemical glucose methods are therefore needed.

Accordingly, a number of procedures and apparatus have been suggested to determine glucose in blood, tissue and other biological samples in vivo and in a non-invasive manner. Existing non-invasive procedures for glucose determination include nuclear magnetic resonance (NMR), electron spin resonance (ESR) and infrared spectroscopy. However, none of these procedures has achieved practical significance. Large and costly equipment is required, which are wholly unsuitable for routine analysis or even for patient self-checking (home monitoring).

One of the most promising approaches for non-invasive glucose monitoring is based on optical techniques. Optical glucose monitoring techniques are particularly attractive in that they are relatively fast, use non-ionizing radiation, and generally do not require consumable reagents. Several optical glucose monitoring techniques have been proposed so far, with varying degrees of success. Several of these techniques are discussed herein as background, however, once again, none of these techniques has attained significant commercial success relative to invasive techniques.

One approach is Near-Infrared (NIR)/Mid-Infrared (MIR) spectroscopy. In infrared spectroscopy, radiation from external light sources is transmitted through or reflected by a body part. Spectroscopic techniques are used to analyze the amount of radiation absorbed at each wavelength by the body part constituents and to compare the absorption data to known data for glucose. Practical implementation of a glucose sensor based on these principles is very difficult and several wavelengths are required. Infrared (IR) spectra are sensitive to physical and chemical factors such as temperature, pH, and scattering. Furthermore, spectroscopy is affected by skin pigmentation, use of medications that absorb various IR wavelengths, alterations in blood levels of hemoglobin or other proteins that absorb IR, changes in body temperature, and alterations in the state of hydration or nutrition. In addition, the NIR spectrum of glucose is very similar to that of other sugars, including fructose, which is often used by diabetics. Therefore, the signal (i.e. the change in the absorption spectrum as a function of glucose concentration) is very small compared to noise and to interference resulting especially from the water spectral absorption and other strongly absorbing components.

Another approach is Raman Spectroscopy. With Raman spectroscopy, Raman spectra are observed when incident radiation is inelastically scattered. The loss or gain of photon energy are independent of the excitation frequency and provide specific information about the chemical structure of the sample. The Raman signal is very weak, requiring long data acquisition time, making the device sensitive to light source fluctuations. Measurements are subject to high background noise because of tissue autofluorescence. Scatter and reabsorption in biological tissues make detection of Raman frequency shifts due to physiological concentrations difficult.

Another spectroscopic approach is based on photoacoustics. In photoacoustic spectroscopy, a laser beam pulse is used to rapidly heat the tissue and generate an acoustic pressure wave that can be measured by a microphone or other transducer. The acoustic signal is analyzed to infer blood glucose concentration. Measurements are affected by chemical interferences from biological molecules as well as physical interference from temperature and pressure changes. Current instruments are complex and sensitive to environmental conditions.

Another optical approach considered of glucose monitoring is based on employing polarimetry. Glucose concentration changes the polarization of light fields. The eye's aqueous humor has been suggested as the medium for this technique as skin is not a feasible site due to its high light scattering properties. However, polarization measurements are affected by optical rotation due to cornea, and by other optically active substances. Other interfering factors include saccadic motion and corneal birefringence. In addition, there is a significant lag between blood glucose changes and glucose changes in intra-ocular fluids, of up to 30 minutes.

Yet, another approach employed for glucose monitoring is based on light scattering. Changes in glucose levels induce changes in light scattering properties, generally, of the skin. U.S. Pat. No. 6,226,089 to Hakamata discloses detecting the intensities of backscattering light generated by predetermined interfaces of an eyeball when a laser beam emitted from a semiconductor laser is projected onto the eyeball in a predetermined position. The absorbance or refractive index of the aqueous humor in the anterior chamber of the eyeball is determined on the basis of the intensities of the backscattering light, and the glucose concentration in the aqueous humor is determined on the basis of the absorbance or refractive index in the aqueous humor. Light scattering effects are evident in the near-infrared range, where water absorption is much weaker than at larger wavelengths (medium- and far-infrared). However, techniques that rely on the backscattered light from the aqueous humor of the eye are affected by optical rotation due to cornea, and by other optically active substances. Other interfering factors include saccadic motion and corneal birefringence. Finally, it should be appreciated that there is often a significant time lag, (e.g., up to 30 minutes) between blood glucose changes and glucose changes of the intra-ocular fluids.

Low-Coherence Interferometry (LCI) is one technique for analyzing skin light scattering properties. Low Coherence Interferometry (LCI) is an optical technique that allows for accurate, analysis of the scattering properties of heterogeneous optical media such as biological tissue. In LCI, light from a broad bandwidth light source is first split into sample and reference light beams which are both retro-reflected, from a targeted region of the sample and from a reference mirror, respectively, and are subsequently recombined to generate an interference signal. Constructive interference between the sample and reference beams occurs only if the optical path difference between them is less than the coherence length of the source.

U.S. Pat. No. 5,710,630 to Essenpreis et al. describes a glucose measuring apparatus for the analytical determination of the glucose concentration in a biological sample and comprising a light source to generate the measuring light, light irradiation means comprising a light aperture by means of which the measuring light is irradiated into the biological sample through a boundary surface thereof, a primary-side measuring light path from the light source to the boundary surface, light receiving means for the measuring light emerging from a sample boundary surface following interaction with said sample, and a secondary-side sample light path linking the boundary surface where the measuring light emerges from the sample with a photodetector. The apparatus being characterized in that the light source and the photodetector are connected by a reference light path of defined optical length and in that an optic coupler is inserted into the secondary-side measurement light path which combines the secondary-side measuring light path with the reference light path in such manner that they impinge on the photodetector at the same location thereby generating an interference signal. A glucose concentration is determined utilizing the optical path length of the secondary-side measuring light path inside the sample derived from the interference signal.

BRIEF SUMMARY

The above-discussed and other drawbacks and deficiencies of the prior art are overcome or alleviated by the measurement system and methodology disclosed herein. Disclosed herein in an exemplary embodiment is a method for determining a characteristic of an analyte in a biological sample, the method comprising: directing broadband light by means of a sensing light path at the biological sample, at a target depth defined by the sensing light path and a reference light path; and receiving the broadband light reflected from the biological sample by means of the sensing light path. The method also includes: directing the broadband light by means of the reference light path at a reflecting device; receiving the broadband light reflected from the reflecting device by means of the reference light path; and interfering the broadband light reflected from the biological sample and the broadband light reflected from the reflecting device. The method further includes: detecting the broadband light resulting from interference of the broadband light reflected from the biological sample and the broadband light reflected from the reflecting device; and modulating an effective light path length of at least one of the reference light path and the sensing light path to enhance interference of the broadband light reflected from the biological sample and the broadband light reflected from the reflecting device. The method continues with: determining a magnitude of change of the effective light path length introduced by the modulating when interference is enhanced; determining a variation in an index of refraction from a ratio of the magnitude of change of the effective light path length and the target depth; and determining the characteristic of the analyte in the biological sample from the variation in the index of refraction.

Also disclosed herein in an exemplary embodiment is a system for determining a characteristic of an analyte in a biological sample, the system comprising: a broadband light source for providing a broadband light; a sensing light path receptive to the broadband light from the broadband light source, the sensing light path configured to direct the broadband light at the biological sample and to receive the broadband light reflected from the biological sample; and a reflecting device. The system also includes: a reference light path receptive to the broadband light from the broadband light source. The reference light path is configured to direct the broadband light at the reflecting device and to receive the broadband light reflected from the reflecting device, the reference light path coupled with the sensing light path to facilitate interference of the broadband light reflected from the biological sample and the broadband light reflected from the fixed reflecting device. The reference light path and the sensing light path cooperating to define a target depth. The system further includes: a detector receptive to the broadband light resulting from interference of the broadband light reflected from the biological sample and the broadband light reflected from the reflecting device; and a modulator associated with at least one of the reference light path and the sensing light path; the modulator, modulating an effective light path length of the at least one of the reference light path and the sensing light path to enhance interference of the broadband light reflected from the biological sample and the broadband light reflected from the reflecting device; and a processing means configured to determine a magnitude of change of the effective light path length introduced by the modulator when interference is enhanced, a variation in an index of refraction from a ratio of the magnitude of change of the effective light path length and the target depth, and the characteristic of the analyte in the biological sample from the variation in the index of refraction.

Further disclosed herein in another exemplary embodiment is a method for determining a characteristic of an analyte in a biological sample, the method comprising: directing broadband light by means of a sensing light path at the biological sample, at a target depth defined by the sensing light path and a reference light path; receiving the broadband light reflected from the biological sample by means of the sensing light path; directing the broadband light by means of the reference light path at a reflecting device; and receiving the broadband light reflected from the reflecting device by means of the reference light path. The method also includes: interfering the broadband light reflected from the biological sample and the broadband light reflected from the reflecting device; detecting the broadband light resulting from interference of the broadband light reflected from the biological sample and the broadband light reflected from the reflecting device; and modulating an effective light path length of at least one of the reference light path and the sensing light path in accordance with a modulator function having a phase component. The method further includes: determining a magnitude of change of the effective light path length introduced by the modulating when the phase component of the modulator function is generally null; determining a variation in an index of refraction from the magnitude of change of the effective light path length and the target depth; and determining the characteristic of the analyte in the biological sample from the variation in the index of refraction.

Further disclosed herein in yet another exemplary embodiment is a system for determining a characteristic of an analyte in a biological sample, the system comprising: a broadband light source for providing a broadband light; and a sensing light path receptive to the broadband light from the broadband light source. The sensing light path is configured to direct the broadband light at the biological sample and to receive the broadband light reflected from the biological sample. The system also includes a reflecting device and a reference light path receptive to the broadband light from the broadband light source. The reference light path is configured to direct the broadband light at the reflecting device and to receive the broadband light reflected from the reflecting device. The reference light path is coupled with the sensing light path to facilitate interference of the broadband light reflected from the biological sample and the broadband light reflected from the fixed reflecting device. The reference light path and the sensing light path cooperating to define a target depth. The system further includes: a detector receptive to the broadband light resulting from interference of the broadband light reflected from the biological sample and the broadband light reflected from the reflecting device; and a modulator associated with at least one of the reference light path and the sensing light path. The modulator, modulating an effective light path length of at least one of the reference light path and the sensing light path in accordance with a modulator function having a phase component. The system further includes a processing means configured to determine: a magnitude of change of the effective light path length introduced by the modulator when the phase component of the modulator function is generally null; a variation in an index of refraction from the magnitude of change of the effective light path length and the target depth; and the characteristic of the analyte in the biological sample from the variation in the index of refraction.

BRIEF DESCRIPTION OF THE DRAWINGS

These and other features and advantages of the present invention may be best understood by reading the accompanying detailed description of the exemplary embodiments while referring to the accompanying figures wherein like elements are numbered alike in the several figures in which:

FIG. 15A depicts a process for fabricating the splitter-modulator module in accordance with an exemplary embodiment;

FIG. 15B depicts a process of fabricating the splitter-modulator module in accordance with an exemplary embodiment;

FIG. 15C depicts a process of fabricating the splitter-modulator module in accordance with an exemplary embodiment;

DETAILED DESCRIPTION OF AN EXEMPLARY EMBODIMENT

Figure 1:
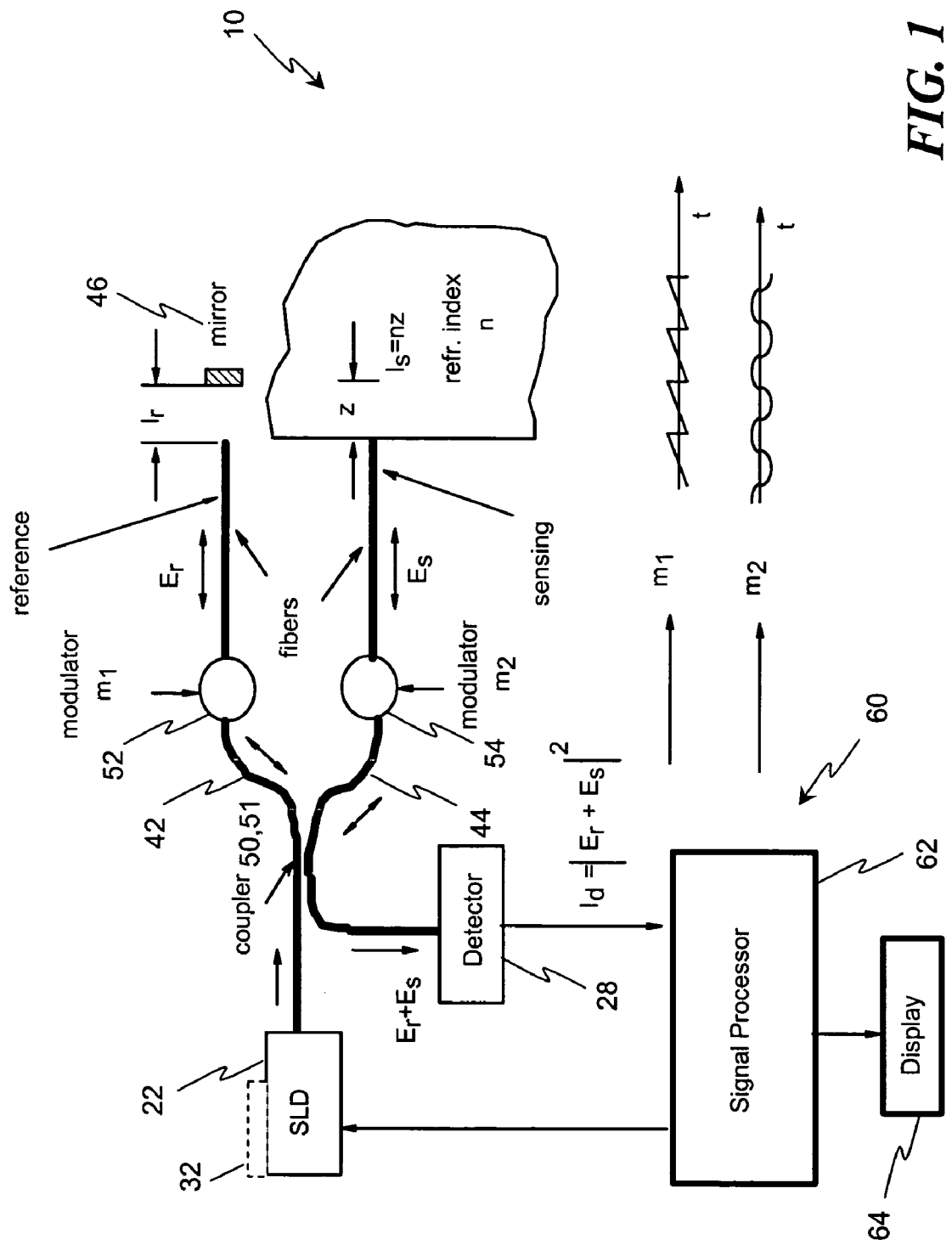
FIG. 1 is a basic all-fiber low-coherence interferometer (LCI)

Disclosed herein, in several exemplary embodiments are high-sensitivity low coherence interferometric (LCI) systems (instruments) for optical metrology, which in an exemplary embodiment are miniaturized for use in a variety of sensing and monitoring applications, including, but not limited to, trace chemical sensing, optical properties and changes thereof, medical sensing such as non-invasive glucose monitoring and others. In an exemplary embodiment, the instrument is miniaturized, using integrated optics components such as waveguides, splitters and modulators on a single substrate such as, but not limited to, a LiNbO3 (Lithium Niobate) chip. The exemplary embodiments may also involve the use of a "circulator" type of optical component, including of a polarizing beam splitter and quarter-wave plate, which can be combined with the light source and detector into a miniature module that prevents optical feedback into the light source while doubling the detected light. Alternatively, instead of the polarizing beam splitter and quarter wave plate one or more isolators and a waveguide coupler may be employed in a similar module to accomplish the same purpose. Disclosed herein in the exemplary embodiments are multiple methodologies and associated systems employed to derive information from the magnitude and/or phase of an interferometric signal.

It will be appreciated that while the exemplary embodiments described herein are suitable for the analysis in comparatively highly scattering, i.e. optically heterogeneous biological samples, optically homogeneous (that is, low-scattering or entirely non-scattering) samples also may be analyzed provided suitable implementations of the embodiments of the invention are employed. It may be further appreciated that the methods discussed herein generally do not allow an absolute measurement of the glucose concentration, but rather a relative measurement from a given baseline. Therefore, calibration to establish a baseline is required. For instance, for one exemplary embodiment, a calibration strip is employed to facilitate calibration. Other methodologies, such as using a sample of known index of refraction, or known glucose concentration may also be employed. The particular glucose concentration in the sample may be determined by any previously known procedure, which allows the determination of the absolute glucose concentration.

It should noted that the light wavelengths discussed below for such methods are in the range of about 300 to about several thousand nanometers (nm), that is in the spectral range from near ultraviolet to near infrared light. In an exemplary embodiment, for the sake of illustration, a wavelength of about 1300 nm is employed. The term "light" as used herein is not to be construed as being limited or restricted to the visible spectral range.

It is well known that the presence of glucose affects the light scattering properties of tissue, and the refractive index denoted as n of the Interstitial Fluid (ISF) and the refractive index of the scattering centers in the tissue—cell membranes, cellular components and protein aggregates. It is also known that a near infrared (NIR) light of a few milliwatts optical power can penetrate the skin harmlessly, whether being delivered directly from the air, a fiber, some appropriate waveguide, or some combination thereof. In the NIR range the refractive index of ISF is about 1.348–1.352, whereas the refractive index of cellular membranes and protein aggregates ranges from about 1.350 to 1.460. Since the tissue under the skin is highly scattering, the light is scattered in all directions, and only a small amount, the so-called ballistic photons, is captured. It is the light from the ballistic photons captured that are employed to produce an interferometric signal. Raising the glucose concentration in the ISF raises the ISF refractive index by approximately $1.52 \times 10^{-6}$ per each mg/dl. Furthermore, the physiological delay of blood glucose transfer from blood to the ISF is of the order of only 2–5 minutes, which makes monitoring of blood glucose in ISF highly practical especially compared to existing methodologies that employ the aqueous humor of the eye.

It will also be noted that for a homogeneously scattering medium for which a specific property such as the refractive index is to be measured, it is sufficient to probe at a single depth, as the desired information can be obtained from the phase of the interferometric signal, presumed to be independent of the amplitude. In this case, an instrument as described herein can be configured for measurement at a single depth. However, if desired, to probe for inhomogeneities (local changes of absorption, reflection, or refractive index), the instrument may be configured to measure both the amplitude and the phase of the interferometric signal as functions of depth. Described herein in a first exemplary embodiment is a system configured to probe at a fixed depth, while later embodiments may be employed for measurement at variable depths and for general imaging purposes. In any case, emphasis is placed on miniaturization, portability, low power and low cost.

Finally, it will also be appreciated that while the exemplary embodiments disclosed herein are described with reference and illustration to glucose measurements, applications and implementations for determination of other characteristics of analytes may be understood as being within the scope and breadth of the claims. Furthermore, the methodology and apparatus of several exemplary embodiments are also non-invasive, and thereby eliminate the difficulties associated with existing invasive techniques. In particular, with respect to detection of glucose concentration, the LCI systems of several exemplary embodiments are configured to be non-invasive, avoiding painful lancets and the like.

Another important consideration is that, as a tool, particularly for medical diagnostic applications, the LCI system of the exemplary embodiments is preferably configured to be easily portable, and for use by outpatients it must be small. Once again, for the purpose of illustration, the LCI system 10 will be described in the context of non-invasive glucose monitoring, capable of detecting the glucose concentration in the dermis by just touching the patient's skin with the instrument. Moreover, the LCI system 10 is configured to be readily hand-held to facilitate convenient measurements by a patient without additional assistance in any location.

Figure 4A:
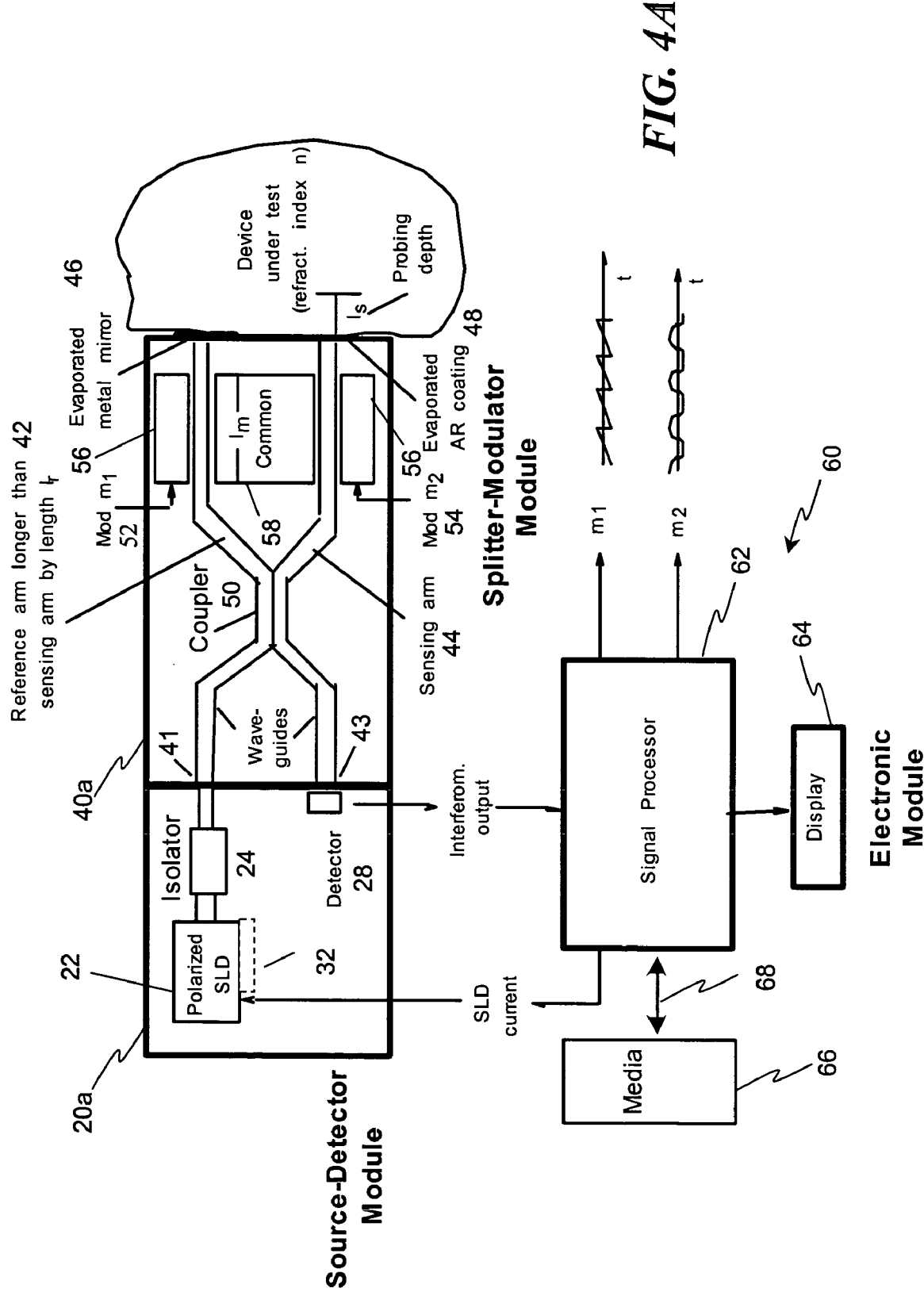
FIG. 4A depicts a minimum configuration interferometer system in accordance with an exemplary embodiment of the invention.

To facilitate appreciation of the various embodiments of the invention reference may be made to FIG. 1, depicting an all-fiber low-coherence interferometer (LCI) system and the mathematical equations developed herein. Referring also to FIG. 4A, in an exemplary embodiment, an LCI system 10 includes, but is not limited to two optical modules: a source-detector module 20a and a splitter-modulator module 40a, and associated processing systems 60. The source-detector module 20a including, but not limited to, a broadband light source 22, such as a super luminescent diode (SLD) denoted hereinafter as source or SLD, attached to a single-mode fiber 23 or waveguide, an isolator 24 configured to ensure that feedback to the broad band light source 22 is maintained at less than a selected threshold. The source-detector module 20a also includes an optical detector 28.

The splitter-modulator module 40a includes, but is not limited to, a waveguide input 41, a waveguide output 43, a splitter/coupler 50, and two waveguide light paths: one light path, which is denoted as the reference arm 42, has adjustable length 1r with a reflecting device, hereinafter a mirror 46 at its end; the other light path, which is denoted as the sensing arm 44, allows light to penetrate to a distance z in a medium/object and captures the reflected or scattered light from the medium. It will be appreciated that the captured reflected or scattered light is likely to be only the so-called "ballistic photons", i.e., those that are along the axis of the waveguide. Provision is also made for one or more modulators 52, 54 in each of the reference arm 42 and sensing arm 44 respectively.

Figure 4B:
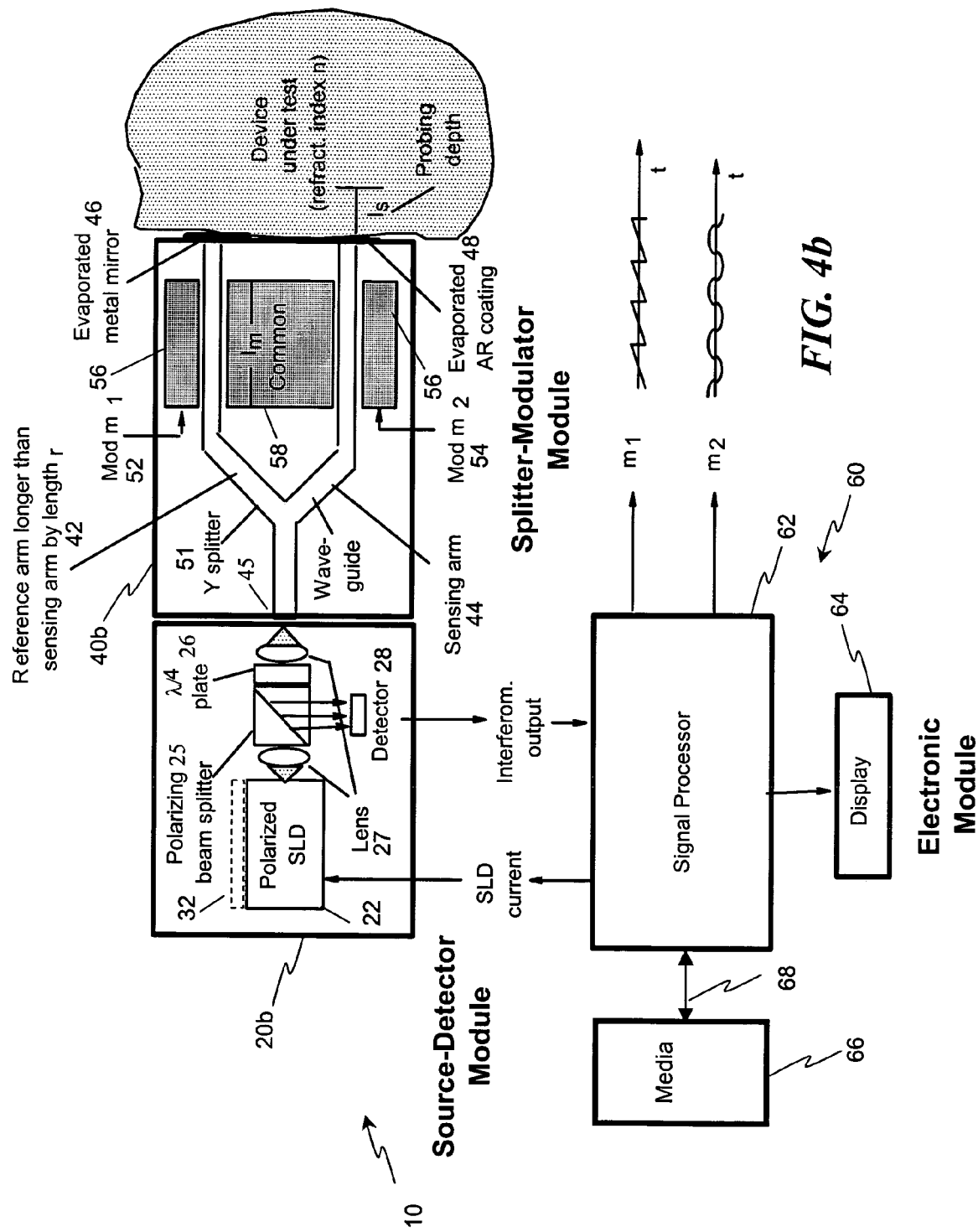
FIG. 4B depicts a configuration of an interferometer system in accordance with an exemplary embodiment of the invention.

Continuing with FIG. 4B as well, in another exemplary embodiment, the source-detector module 20b includes, but is not limited to, a polarized broad-band light source 22, attached to a single-mode fiber 23. The source-detector module 20b also includes a polarizing beam splitter 25 with an quarter wave plate 26 employed to ensure a selected polarization configured to facilitate ensuring that feedback to the broad band light source 22 is maintained at less than a selected threshold. The source-detector module 20b also includes an optical detector 28.

The splitter-modulator module 40b of this embodiment includes, but is not limited to, a waveguide inputs/output 45, a Y-splitter-combiner 51, and the two waveguide arms: reference arm 42, and sensing arm 44. Once again, provision is also made for one or more modulators 52, 54 in each of the reference arm 42 and sensing arm 44 respectively.

It will be appreciated that while certain components have been described as being in selected modules, e.g., 20, 40, such a configuration is merely illustrative. The various components of the LCI system 10 may readily be distributed in one or more various modules e.g., 20, 40 as suits a given implementation or embodiment. Furthermore, in an exemplary embodiment the waveguide arms 42, 44 and/or fibers 23 are configured for single-transverse-mode transmission, and preferably, but not necessarily, polarization-maintaining waveguides or fibers. Furthermore it will be appreciated that in any of the exemplary embodiments disclosed herein the waveguide and/or fiber tips of each component joined are configured e.g., angled-cleaved in a manner to minimize reflection at the junctions.

In order to perform the prescribed functions and desired processing, as well as the computations therefore (e.g., the computations associated with detecting and utilizing the interference signal, and the like), the LCI system 10, and more particularly, the processing system 60, may include, but is not limited to a computer system including central processing unit (CPU) 62, display 64, storage 66 and the like. The computer system may include, but not be limited to, a processor(s), computer(s), controller(s), memory, storage, register(s), timing, interrupt(s), communication interface(s), and input/output signal interfaces, and the like, as well as combinations comprising at least one of the foregoing. For example, computer system may include signal input/output for controlling and receiving signals from the source-detector module 20 as described herein. Additional features of a computer system and certain processes executed therein may be disclosed at various points herein.

The processing performed throughout the LCI system 10 may be distributed in a variety of manners as will also be described at a later point herein. For example, distributing the processing performed in one ore more modules and among other processors employed. In addition, processes and data may be transmitted via a communications interface, media and the like to other processors for remote processing, additional processing, storage, and database generation. Such distribution may eliminate the need for any such component or process as described or vice versa, combining distributed processes in a various computer systems. Each of the elements described herein may have additional functionality that will be described in more detail herein as well as include functionality and processing ancillary to the disclosed embodiments. As used herein, signal connections may physically take any form capable of transferring a signal, including, but not limited to, electrical, optical, or radio.

The light reflected from the reference mirror 46 (Electric field $E_r$) in the reference arm 42 and the light reflected or scattered from depth z within the biological sample (Electric field $E_s$) in the sensing arm 44 are combined at the optical detector 28, whose output current is proportional the combined electric fields. For example, in one instance, the output of the detector is proportional to the squared magnitude of the total electric field $E_t = E_r + E_s$.

The detector current $I_d$ is given by:

$$I_d = \eta |E_r + E_s|^2 = I_r + I_s + 2\sqrt{I_r I_s} |G(\tau)| \cos 2\pi v_o \tau \quad (1)$$

where $\eta$ is the detector quantum efficiency (typically <1), $I_r = \eta E_r \cdot E_r^*$ is the detector current due to $E_r$ alone, $I_s = \eta E_s \cdot E_s^*$ is the detector current due to $E_s$ alone, and the * represents the complex conjugate. $E_r \cdot E_r^*$ and $E_s \cdot E_s^*$ represent the optical power in the reflected reference field and reflected sensing field, respectively. The quantity $\tau$ is the time delay between the reference field $E_r$ and sensing field $E_s$, and is given by:

$$\tau = \frac{l_r}{c} - \frac{z}{c/n} = \frac{l_r - l_s}{c} = \frac{\Delta l}{c} \quad (2)$$

where $l_s = nz$ and $\Delta l = l_r - l_s$ and where $\Delta l$ is the optical path difference between the reference $l_r$ and sensing $l_s$ arms 42, 44, z is the selected or desired target depth in the biological sample, n is the index of refraction in the sample, and c is the speed of light. Also in Equation (1), $v_o$ is the center frequency of the light source 22, and $G(\tau)$ it the cross-correlation function between the reference and sensing fields. Its magnitude is given by:

$$|G(\tau)| = \exp\left[-\left(\frac{\pi \Delta v \tau}{2\sqrt{\ln 2}}\right)^2\right] \quad (3)$$

where $\Delta v$ is the FWHM (full width half maximum) frequency bandwidth of the light source 22.

The last term in Equation (1), the interference term, is the quantity of interest denoted as $i_o$:

$$i_o(\tau) = 2\sqrt{I_r I_s} |G(\tau)| \cos 2\pi v_o \tau \quad (4)$$

It is convenient to express the interference term $i_o$, in terms of the center wavelength $\lambda_o$ and the path difference $\Delta l$ associated with the interferometer, instead of the frequency and time delay. Therefore, using $v_o \lambda_o = c$, where c is the speed of light in vacuum, $\Delta v$ may be written in terms of the wavelength FWHM bandwidth $\Delta \lambda$, to obtain:

$$i_o(\Delta l) = 2\sqrt{I_r I_s}\, |G(\Delta l)|\cos\phi_s \text{ where } \phi_s = \frac{2\pi}{\lambda_o}\Delta l \text{ and} \quad (5)$$

$$|G(\Delta l)| = \exp\left[-\left(\frac{\Delta l}{L_c}\right)^2\right] \quad (6)$$

where $L_c$ is the coherence length of the light source and is given by $$L_c = \frac{2\sqrt{\ln 2}}{\pi}\frac{\lambda_o^2}{\Delta\lambda} = 0.44\frac{\lambda_o^2}{\Delta\lambda}. \quad (7)$$

Figure 2A:
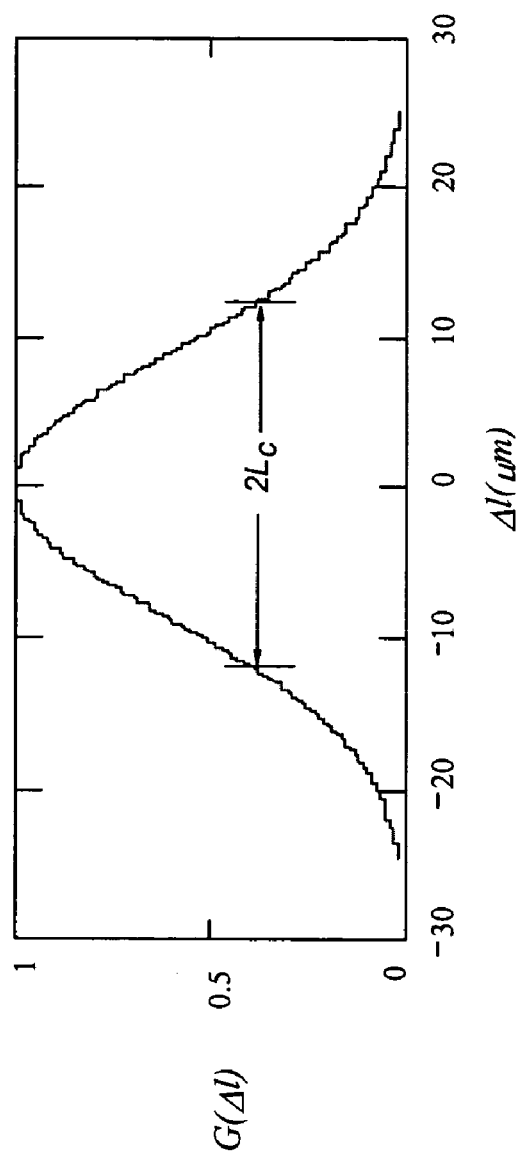
FIG. 2 depicts a plot of the envelope function $G(\Delta l)$ and of the interference signal $G(\Delta l)\cos \phi_s$.
Figure 2B:
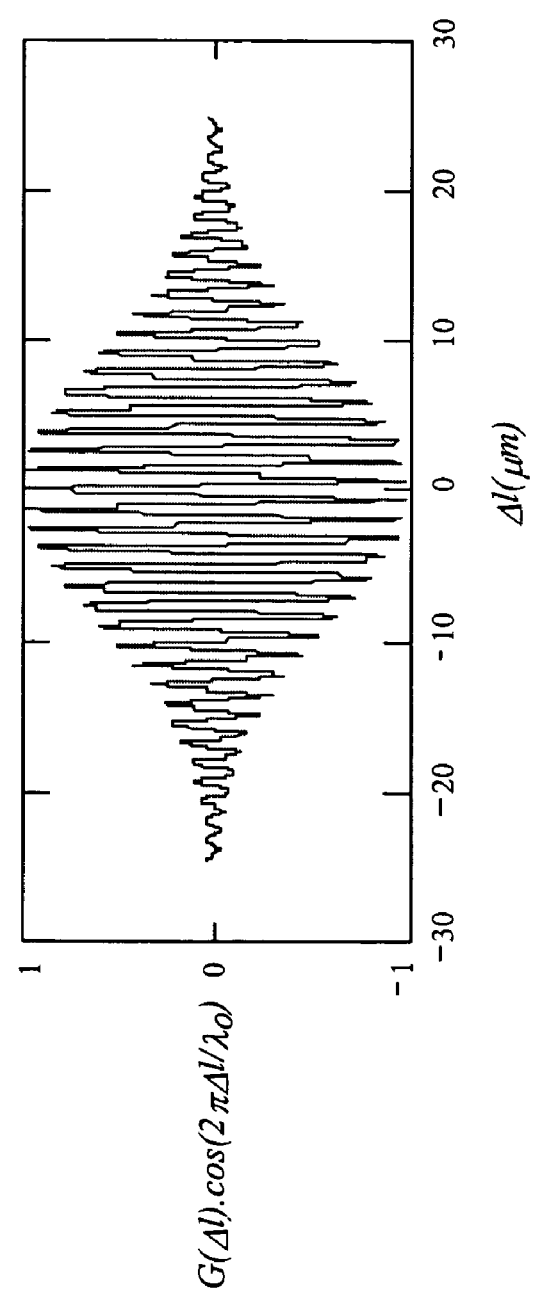

A plot of the envelope function $G(\Delta l)$ and if the interference signal $G(\Delta l)\cos\phi_s$ is shown in FIGS. 2A and 2B respectively, for an interferometer with a light source 22 having center wavelength $\lambda_o=1.3$ μm and FWHM bandwidth $\Delta\lambda=60$ nm (coherence length $L_c=12.4$ μm). The detected interference signal exhibits a maximum when the interferometer is balanced, i.e., when the path difference $\Delta l=0$. As the system 10 becomes increasingly unbalanced, e.g., $\Delta l \neq 0$, the interference signal exhibits maxima and minima of decreasing amplitude over a range determined by $\Delta l$.

It will be appreciated that the interference signal $i_o$ exhibits significant amplitude only over a spatial window of approximately twice the coherence length $L_c$. As the optical bandwidth increases, the coherence length $L_c$ decreases and the spatial measurement window narrows. Thus, LCI provides a means for probing samples at precisely defined locations within the samples.

Figure 3:
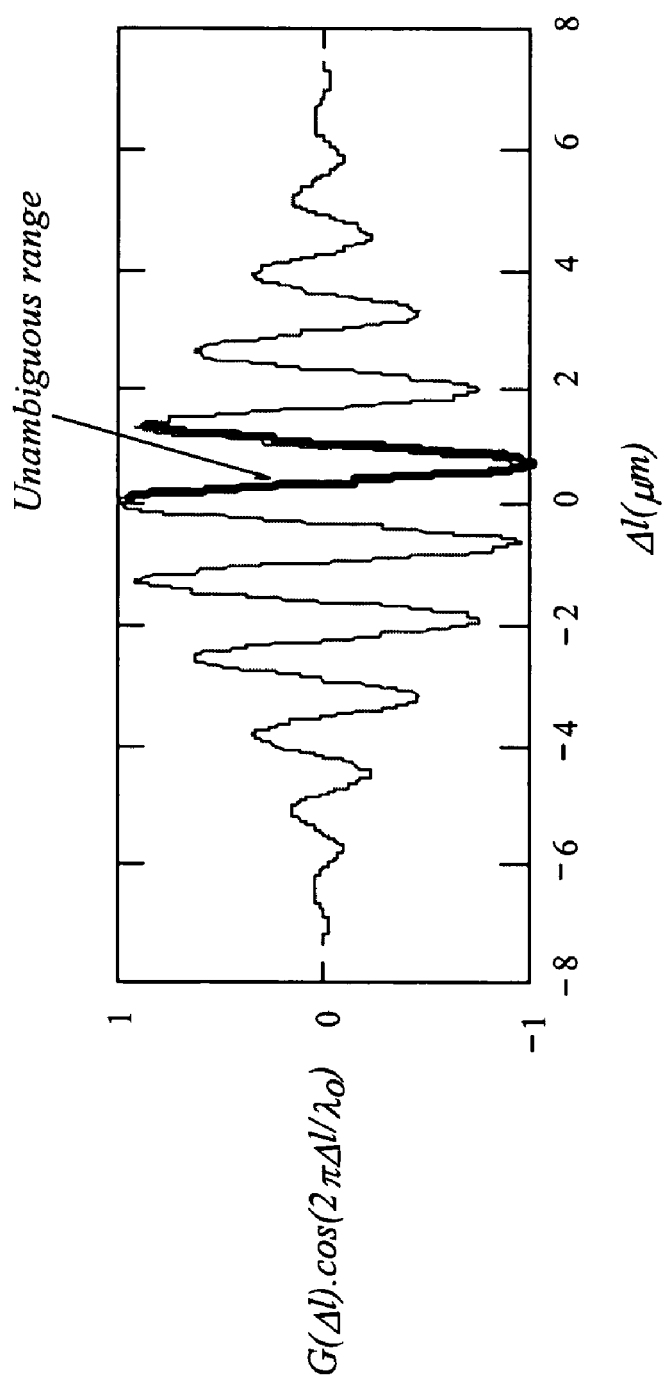
FIG. 3 depicts a range of unambiguous measurement for a periodic interference signal.

It is noteworthy to appreciate that the phase, $\phi_s$, of the interference signal $i_o$ changes by $2\pi$ (from a maximum to a minimum then to another maximum) as $\Delta l$ varies from 0 to $\lambda_o$. Therefore, a small change in $\Delta l$ results in a substantial phase change. It will be further appreciated that the phase of the interference signal $i_o$ is highly sensitive to small changes of optical properties of the mediums, such as refractive indices, or depth z. Thus, while moderate to large changes may readily be observed by measuring the magnitude of the envelope $G(\Delta l)$, small changes are best detected by measuring the phase $\phi_s$ of the interference signal $i_o$. It will be further appreciated that all the desired information is contained in the range from 0 to $2\pi$. For values of $\Delta l > \lambda_o$, the interference signal $i_o$ is repetitive. Thus, the range from 0 to $2\pi$ as indicated in FIG. 3 is a range for which the desired information can be measured without ambiguity. It may also be noted however, that if the coherence length $L_c$ is short enough that the amplitude difference between the main peak and secondary peaks is measurable, then phase measurement beyond $2\pi$ may also be realized.

Therefore, it will be readily be appreciated that there are two types of information, which can be derived from the interference signal $i_o$: the envelope $G(\Delta l)$, or its peak $G(\Delta l=0)$, which may represent scattering, reflection, and absorption; and the more sensitive changes in $\cos\phi_s$ due to small optical property changes in the sample. In order to make any such measurements, it is first preferable to separate the DC components $I_r$ and $I_s$ from $G(\Delta l)$ and $\cos\phi_s$ in the interferometric signal $i_o$ described in Equation (5). In one or more exemplary embodiments of the invention, several methodologies are disclosed for extracting the pertinent information from the interference signal $i_o$ described in Equation (5). A first methodology addresses a ratio of an effective light path length and a variation thereof for generating the interference signal, while others addresses detecting the phase, or more specifically a particular phase shift $\phi_s$ of the interference signal $i_o$ introduced in the sample.

Continuing now with FIGS. 4A and 4B, the first approach uses a periodic ramp applied to one of the modulators 52, 54. Another approach, also called a homodyne methodology employs a sine wave applied to one of the modulators 52, 54. It will be appreciated that while for the purposes of description of one or more exemplary embodiments, a particular modulator in a particular arm of the LCI system 10 is described as including a modulator, other configurations are conceivable. For example, while the description of an exemplary embodiment calls for modulation of the length of the reference arm of the LCI system 10, manipulation of other optical lengths in the LCI system 10 may be employed for establishing the interference signal and the level of modulation required to achieve the particular desired result.

Using one of the modulators, ($m_1$ 52, for example) or an equivalent means, a ramp modulation is applied to one of the interferometer arms, the reference arm 42, for example, changing $l_r$ over a distance from $-b$ to a over a time period T, such that:

$$\Delta l = \frac{a}{T}t - b \text{ for } t < 0 < T \quad (8)$$

and if periodic, $$\Delta l(t+T) = \Delta l(t).$$

This yields:

$$G(\Delta l)\cos\left(\frac{2\pi}{\lambda_o}\Delta l\right) = \exp\left[-\left(\frac{\frac{a}{T}t - b}{L_c}\right)^2\right]\cos\left[\frac{2\pi}{\lambda_o}\left(\frac{a}{T}t - b\right)\right] \quad (9)$$

and, $$i_o(t) = 2\sqrt{I_r I_s}\cos(2\pi f_c t - \phi_c) \quad (10)$$

where $$f_c = \frac{a}{\lambda_o T} \text{ and } \phi_c = \frac{2\pi b}{\lambda_o}.$$

Figure 5:
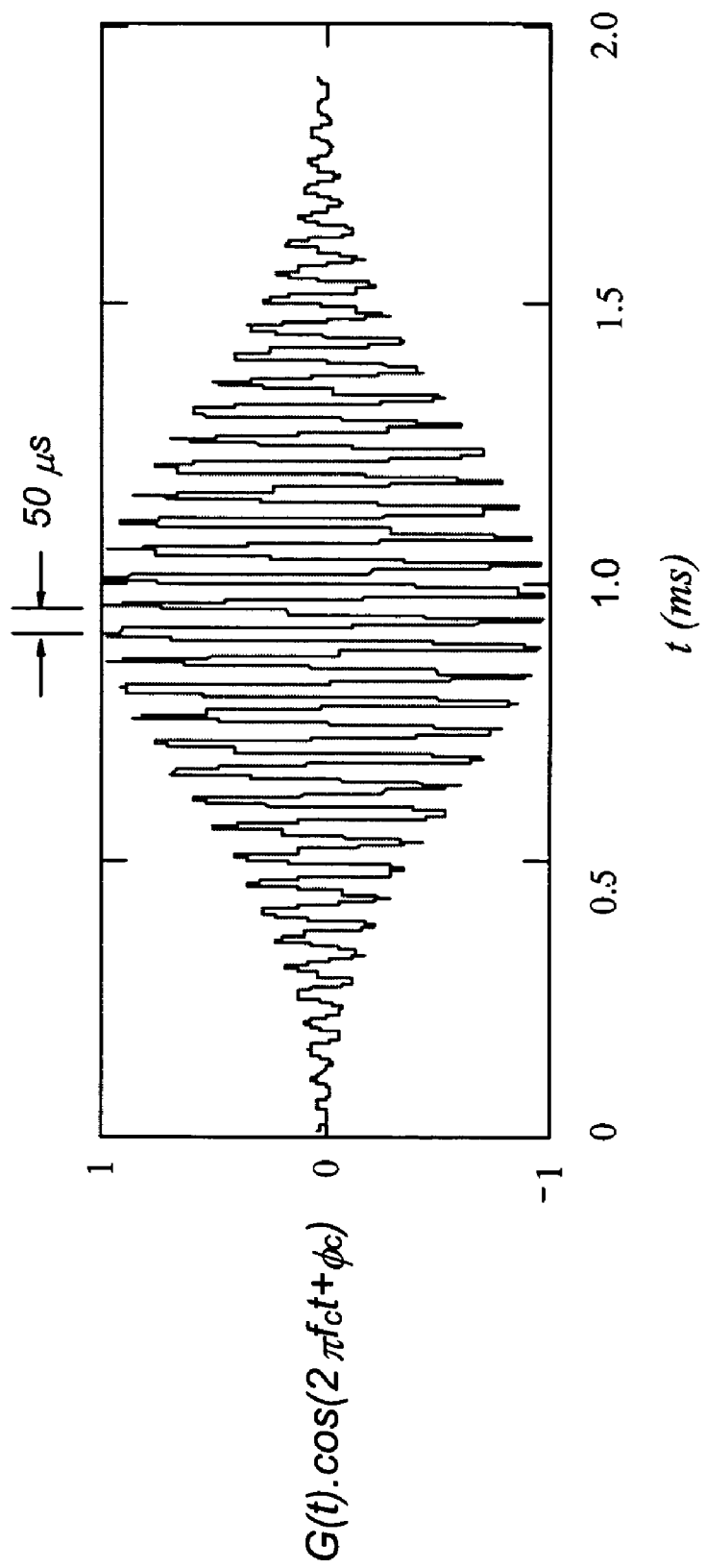
FIG. 5 depicts a plot of the interference signal for a single ramp.

The resultant of the modulation represents a sine wave of frequency $f_c$ with an arbitrary phase $\phi_c$ determined by b, which is amplitude-modulated (AM) by the $G(\Delta l)$ envelope function, now also a function of time. FIG. 5 depicts a plot of the function in equation (9) for a single ramp sweeping over $\pm 2L_c$ for the light source example used earlier, with $a=4L_c$ and $b=2Lc$), and for $T=1.9$ ms, we get $f_c=20$ KHz. When the ramp function used for modulation is periodic, this signal repeats with the periodicity of the ramp function. Advantageously, the interference signal may be readily envelope-detected in similar fashion to an AM receiver signal, to obtain $G(\Delta l)$, and peak-detected, preferably in an iterative fashion, to yield $G(\Delta l=0)$, which can then be digitized for further processing.

As discussed earlier, the most sensitive interferometric information can be derived from the phase variations of the interference signal $i_o$ resulting from small changes in material properties. For example, referring to Equation (2), a small change $\Delta n$ in the refractive index n, at a depth z in the sample, will result in a corresponding change in $\Delta l$ by the amount $z\Delta n$. To analyze such a change by a ramp modulation method as described above, the ramp described above in Equation (8), is applied to the modulator $m_1$ 52, but, in addition, an extra optical path length $z\Delta n$ is also included to facilitate addressing the phase shift in the interference signal $i_o$, yielding:

$$\Delta l = a/Tt - b + z\Delta n, \text{ for } 0 \leq t \leq T \text{ and } \Delta l(t+T) = \Delta l(t) \quad (11)$$

and writing $G(\Delta l) \sim 1$ for $a \sim \lambda_o$, yields:

$$i_o(t) = 2\sqrt{I_r I_s} \cos(2\pi f_c t - \phi_c + \phi_n), \text{ where } \phi_n = \frac{2\pi}{\lambda_o} z\Delta n. \quad (12)$$

Figure 7B:
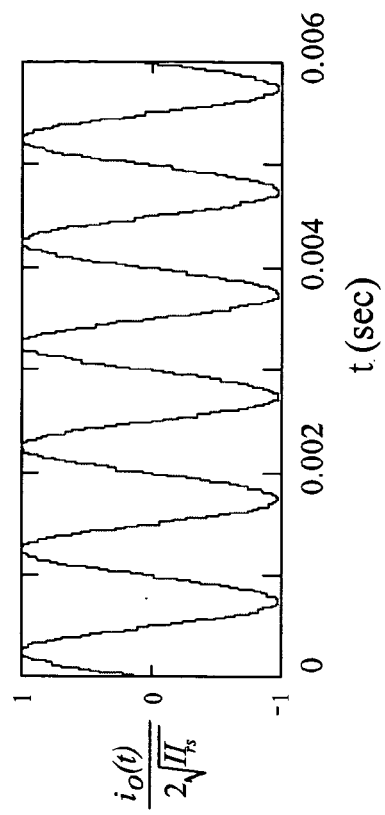
FIG. 7B depicts an interference signal corresponding to $\Delta n=0.0003$ at a 1 mm depth.
Figure 7A:
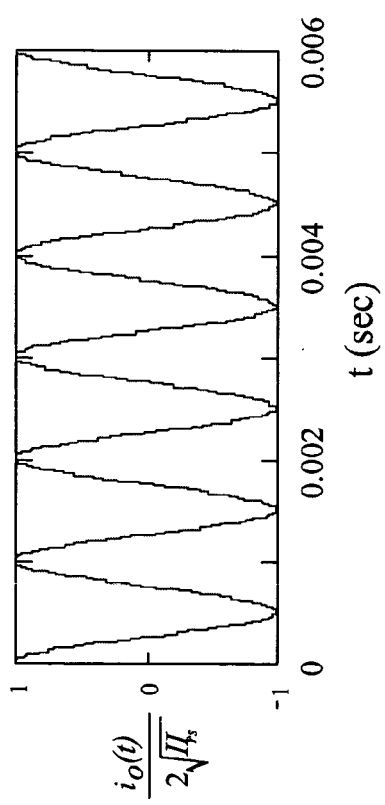
FIG. 7A depicts an interference signal corresponding to $\Delta n=0$ at a 1 mm depth.

This interference signal $i_o$ is illustrated in FIGS. 9A and B for a 1 mm depth, where FIG. 7A corresponds to $\Delta n = 0$, and FIG. 7B corresponds to $\Delta n = 0.0003$, clearly indicating the phase shift due to $\Delta n$. The calculated phase shift $\phi_n$ is 1.5 rad (about 80 deg). For glucose concentration monitoring applications such a phase shift would correspond to a glucose concentration of about 197 mg/dl (near the upper limit in humans). Advantageously, this example provides a clear indication of the sensitivity of the phase measurement.

Figure 6:
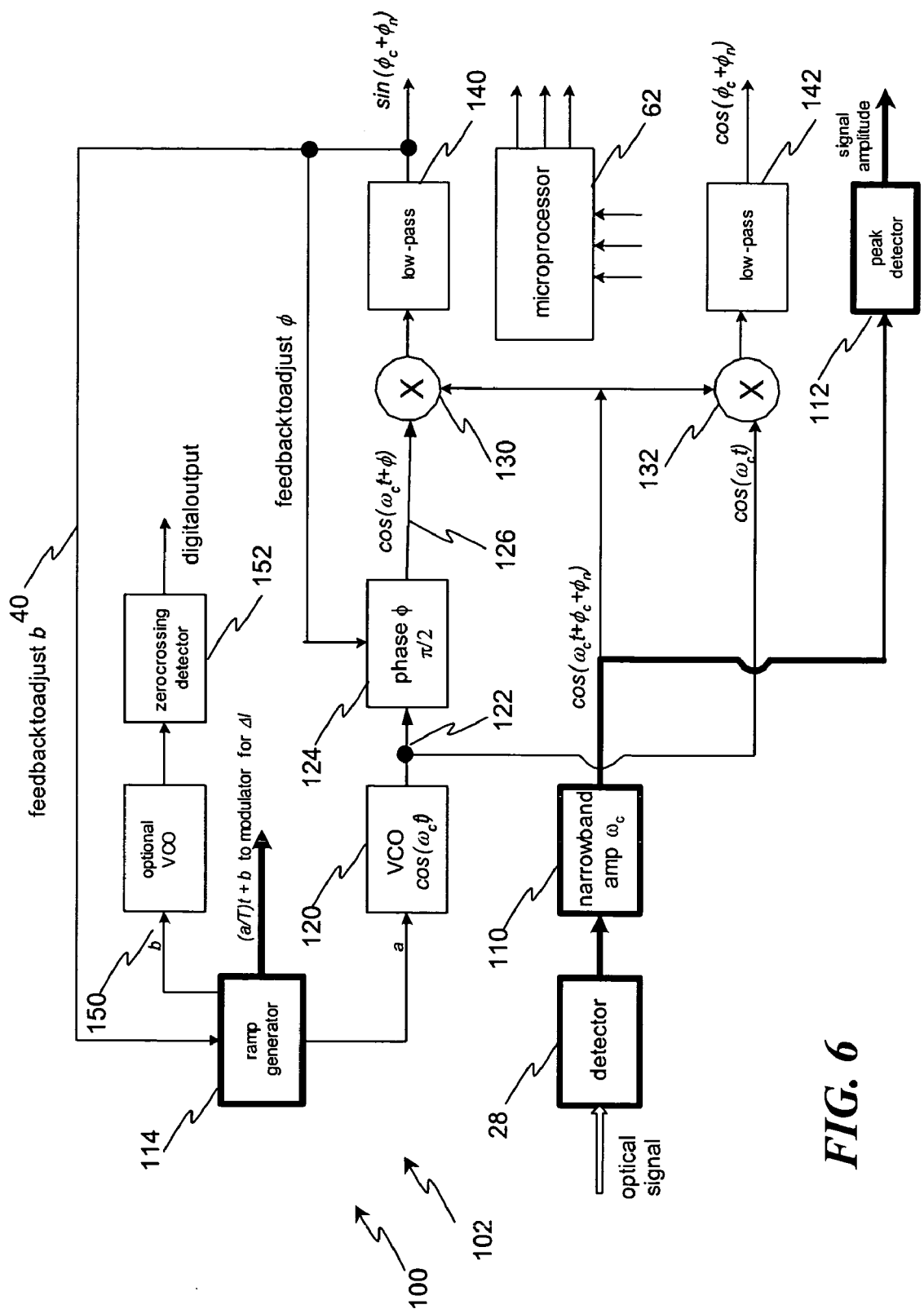
FIG. 6 depicts an a simplified block depicting a detection scheme employing ramp modulation.

The phase shift of interference signal $i_o$ may readily be detected using a homodyne process 101 such as depicted in the block diagram of FIG. 6, which produces output signals proportional to the sine and cosine of the phase shift to be measured. In an exemplary embodiment, the change in $\Delta l$ produced by the ramp modulation generates the interferometric signal $i_o$ in the form of a sine wave, $\cos(\omega_c t + \phi_c + \phi_n)$ as in Equation (12), with an additional phase shifting component, denoted $\phi_n$ resulting from the change in the refractive index, $\Delta n$. At the same time, the parameter a of the ramp modulator 114 is applied to a voltage control oscillator (VCO) 120, configured to generate a sinusoidal function at a frequency $\omega_c$ proportional to the magnitude a from the ramp modulation. In an embodiment, a closed loop controller is employed to facilitate determination of $\phi_n$ as will be described herein. The sinusoidal function, $\cos(\omega_c t)$ 122 from the VCO 120 is phase shifted with phase angle $\phi$, as depicted at phase shifting process 124. The phase angle $\phi$ is set to $\pi/2$, to facilitate formation of quadrature sinusoidal signals. The phase-shifted sinusoid 126 is applied to a first multiplying demodulator 130 configured for the loop closure and denoted as a lock-in amplifier. The sinusoidal function $\cos(\omega_c t)$ 122 from the VCO 120 (without the phase shift $\phi$) is also applied to a second multiplying demodulator 132. Similar to the earlier embodiments, the interferometric signal $i_o$ from the optical detector 28 is amplified and filtered through a narrow band filter 110 around $\omega_c$, to extract the signal $\cos(\omega_c t + \phi_c + \phi_n)$, which is then applied to both multipliers 130 and 132 for multiplication by the sinusoidal signal 122 and the phase shifted sinusoidal signal 126. Using the relation $\cos(x) \cos(y) = 0.5 \cos(x+y) + 0.5 \cos(x-y)$, it will be appreciated that the output of the first multiplier 130 contains a term at frequency $2\omega_c$ and a DC term $\cos(\phi_c + \phi_n - \phi)$. Advantageously, the DC term $\cos(\phi_c + \phi_n - \phi)$ may be readily extracted by low-pass filtering as depicted at filtering process 140, and becomes $\sin(\phi_c + \phi_n)$ if $\phi = \pi/2$. Similarly, for the second multiplier 132, following similar low-pass filtering at process 142, the dc term is $\cos(\phi_c \phi_n)$. Thus, after filtering the following two dc output signals are obtained:

from the first modulator: $I_{LP} = \sqrt{I_r I_s} \sin(\phi_c + \phi_n)$ and $\quad (13)$ from the lower modulator: $I_{LP} = \sqrt{I_r I_s} \cos(\phi_c + \phi_n)$. $\quad (14)$ It will be readily appreciated that both signals i.e., sine and cosine, contain the desired information, but the first provides better sensitivity to small $\Delta n$ changes. Preferably, both signals e.g., Equations 13 and 14, are used with their signs being compared to determine the quadrant in which the phase is located to properly obtain the index change. For example, for phase shifts determined to be between 0 and $\pi/2$, both signals are positive and increase or decrease in opposite manner. For phase shifts between $\pi/2$ and $\pi$, they have opposite signs. For phase shifts between $\pi$ and $3\pi/2$, both are negative, and for phase shifts between $3\pi/2$ and $2\pi$, they have opposite sign.

Moreover, while the sine signal is preferably employed because it exhibits greater sensitivity for determining the phase (for example for small phase shifts), it should also be appreciated that advantageously, when the phase is precisely determined, the cosine term provides a precise measure of the magnitude. In other words, with the phase known, the precise peak of the particular period of the cosine term may be ascertained. This approach of determining phase and then the magnitude facilitates determination of the magnitude with greater precision and accuracy than can be achieved with envelope detection methodologies often employed for peak detection.

Therefore, by measuring the two outputs and observing their signs, the phase and magnitude can be unambiguously ascertained for the range from 0 to $2\pi$. It is noteworthy to appreciate that this $2\pi$ limitation applies only if the variations of $G(\Delta l)$ [i.e., $G(t)$] are so small that the difference between the main peak (the absolute peak) and the adjacent ones is not readily measurable. If that difference is measurable, then it is possible to use the above algorithm, together with envelope detection, to ascertain the absolute peak, as well as the secondary peaks, and thus phase shifts in excess of $2\pi$ without ambiguity. Moreover, this would be possible if the coherence length $L_c$ is short enough to enable the relative measurements of the peaks and the identification of the absolute peak (see FIG. 3 as an example).

The index of refraction change $\Delta n$ can be retrieved in several ways. One methodology involves setting the value of $b = 0$ (and thus $\phi_c = 0$) and measuring the values for Equations (13) or (14) directly. Another methodology is to adjust/manipulate the value of b, using a feedback implementation, to result in a change to $\phi_c$ until the sine function of Equation (13) is nulled. When a null is achieved $\phi_c = -\phi_n$, which directly yields:

$$\Delta n = -\frac{b}{z} \quad (15)$$

where z is the selected target probing depth and b is the magnitude of the change in optical path length introduced to balance the interferometer of the LCI system 10. For example, if the value of $\phi_c$ required for nulling is ascertained to be 5° (0.0873 radians) for $\lambda_o = 1.3$ μm, it may be ascertained that (from $\phi = 2\pi b/\lambda_o$) the value of b for nulling to be 0.018 μm, resulting in $\Delta n = 1.8 \times 10^{-5}$ at $z = 1$ mm. In one exemplary embodiment, a voltage proportional to b is transmitted to an optional VCO 150 to generate a sine wave of frequency proportional to b. That frequency may then be converted to a digital signal by means of an optional zero-crossing detector 152 for further utilization or display.

The expression of Equation (15) also indicates that greater sensitivity is obtained by probing deeper into the sample. Conversely, due to scattering and absorption in the probed sample e.g., tissue, the magnitude of the returned signal (Electric field $E_s$) and thus the interferometric signal $i_o$, is reduced at greater depth in the sample. However, it is also well known that if a signal is periodic, that signal may be retrieved by means of a high-gain narrow-bandwidth amplifier (at the expense of measurement time). Similarly, it can be retrieved by means of autocorrelation, again, at the price of measurement time. Thus, it may be inferred that, by using the phase detection methodology disclosed herein, the measurement sensitivity is, substantially independent of the magnitude of the interferometric signal $i_o$.

Figures 8A, 8B:
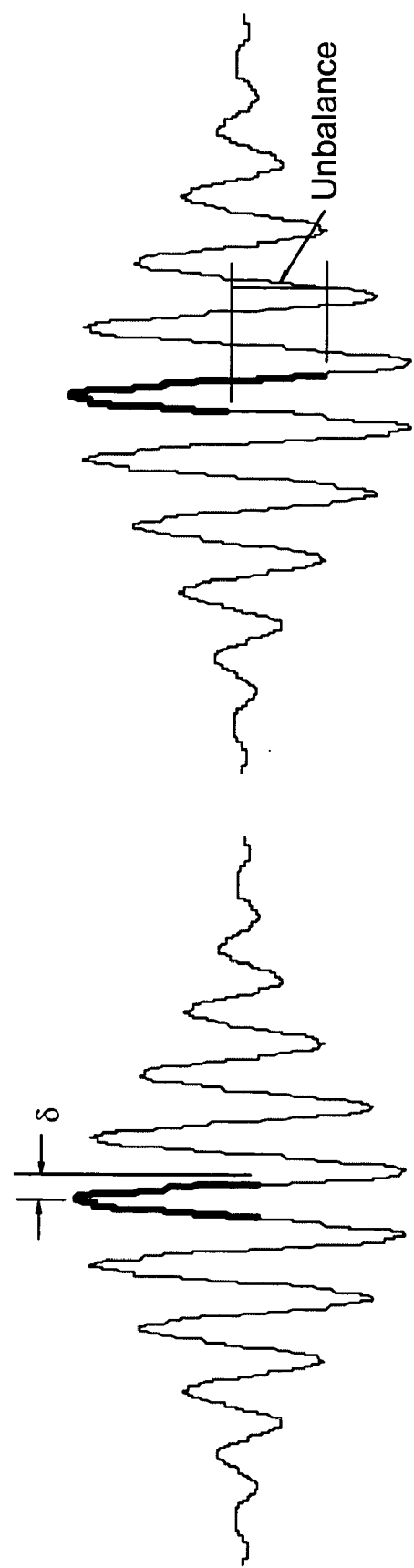
FIG. 8A shows a balanced interferometric signal resultant from sinusoidal modulation depicting a heavy portion oscillating at the frequency f over the peak.
FIG. 8B shows an unbalanced interferometric signal, and a shifted modulation pattern.

Turning now to another exemplary embodiment of the invention, in this case, the phase shift of the interference signal $i_o$ is determined utilizing a sinusoidal modulation technique. A small sine wave signal of amplitude $\delta$ and frequency f is applied to another modulator 54 ($m_2$ for example in FIGS. 4A and 4B in this instance). It causes $\Delta l$ to change as $\delta \cos \omega t$, where $\omega=2\pi f$, and forms a modulation pattern on the balanced interferometric signal such that it exhibits a "wiggle" or rides back and forth at the frequency f over the peak as shown by the heavy portion of the waveform in FIG. 8A. When the interferometer becomes unbalanced by virtue of a change in a material property, the modulation pattern (the heavy portion of the waveform) shifts resulting in the asymmetry as shown in FIG. 8B by virtue of the optical path change $z\Delta n$. Therefore, in an exemplary embodiment, for maintaining a controllable reference phase, provision is made to apply a fixed voltage to modulator $m_1$ 52 with a fixed displacement b and resulting in a phase shift $\phi_c$ as in the previous case.

Therefore, the general form of $\Delta l$ at a given depth z with the sinusoidal modulation can be written as:

$$\Delta l = z\Delta n + b + \delta \cos \omega t \quad (16)$$

and the general form of $\phi_s$ is:

$$\phi_s = \frac{2\pi}{\lambda_o}z\Delta n + \frac{2\pi}{\lambda_o}b + \frac{2\pi}{\lambda_o}\delta\cos\omega t = \phi_n + \phi_c + \phi_\delta\cos\omega t \quad (17)$$

where $\omega=2\pi f$ and $\phi_\delta = 2\pi\delta/\lambda_o$.

Taking the cosine of the equation and converting yields:

$$\cos \phi_s = \cos(\phi_n+\phi_c)\cos(\phi_\delta \cos \omega t) - \sin(\phi_n+\phi_c)\sin(\phi_\delta \cos \omega t). \quad (18)$$

The resultant is a phase-modulated signal, which can be expanded into the Fourier-Bessel series, using:

$$\cos\left(\frac{2\pi}{\lambda_o}\delta\cos\omega t\right) = J_o\left(\frac{2\pi}{\lambda_o}\delta\right) + \sum_n (-1)^n 2J_{2n}\left(\frac{2\pi}{\lambda_o}\delta\right)\cos 2n\omega t \quad (19)$$

$$\sin\left(\frac{2\pi}{\lambda_o}\delta\cos\omega t\right) = \sum_n (-1)^{n+1} 2J_{2n-1}\left(\frac{2\pi}{\lambda_o}\delta\right)\sin(2n-1)\omega t \quad (20)$$

where $J_n(x)$ is the Bessel function of the first kind of argument x and integer order n.

Substituting Equations (18), (19) and (20) into Eq (5) for $\cos \phi_s$, the interferometric signal now includes a DC term $J_o$, and an infinite number of harmonics $J_1$, $J_2$, $J_3$, etc. of decreasing magnitude. We keep the lowest terms by filtering through a low-pass filter, a filter centered at f and one centered at 2f, respectively. We obtain the following outputs:

$$I_{oo} = 2\sqrt{I_r I_s}J_o(\phi_\delta)\cos(\phi_c+\phi_n) \text{ DC term} \quad (21)$$

$$i_{o1}(t) = 4\sqrt{I_r I_s}J_1(\phi_\delta)\sin(\phi_c+\phi_n)\cos \omega t \text{ Fundamental term} \quad (22)$$

$$i_{o2}(t) = 4\sqrt{I_r I_s}J_2(\phi_\delta)\cos(\phi_c+\phi_n)\cos 2\omega t \text{ Second harmonic term} \quad (23)$$

where $G(\Delta l) \approx 1$, since $\Delta l << L_c$.

It is noteworthy to appreciate that the DC term $I_{oo}$ includes the same information with respect to the argument of interest $\phi_n$ as the second harmonic term $i_{o2}(t)$ and may be employed for ascertaining $\phi_n$. However, it is not as stable as $i_{o2}(t)$ and is subject to drift and other environmental factors. Furthermore, the DC term is not readily separable from the other detector DC components $I_r$ and $I_s$. On the other hand, $i_{o1}(t)$ and $i_{o2}(t)$ are locked to the oscillator frequency, which can be controlled accurately. Therefore, it is preferred that $i_{o1}(t)$ and $i_{o2}(t)$ are selected as the interferometer outputs. The amplitude of the fundamental and second harmonic terms may be ascertained, by various methodologies including, but not limited to, lock-in detection, multiplication and filtering as follows:

$$I_{o1} = 2\sqrt{I_r I_s}J_1(\phi_\delta)\sin(\phi_c+\phi_n) \quad (24)$$

$$I_{o2} = 2\sqrt{I_r I_s}J_2(\phi_\delta)\cos(\phi_c+\phi_n). \quad (25)$$

Figure 9:
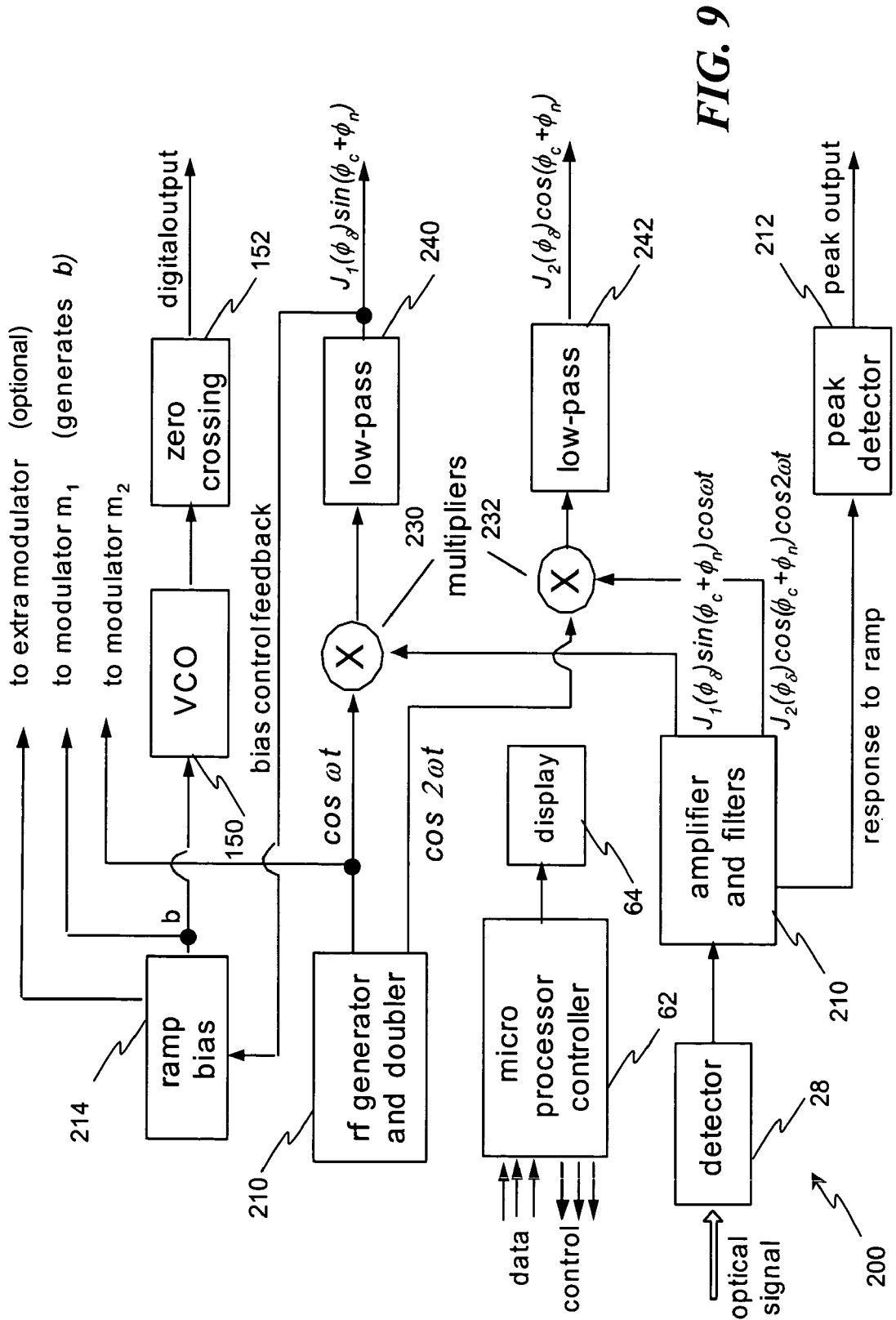
FIG. 9 depicts an implementation of a sinusoidal modulation or homodyne detection scheme.

FIG. 9 depicts an implementation of a sinusoidal modulation and detection or homodyne methodology shown generally as 200. Elements similar to earlier embodiments are similarly referenced but incremented by one hundred. A source 210 generates a sine wave denoted $\cos \omega t$ of frequency f and second one of frequency 2f locked to the first one (for example, by means of a frequency doubler). In an exemplary embodiment a frequency f of about 100 KHz is employed, however, it will be evident that other frequencies may readily be utilized depending upon a particular implementation and application of the LCI system 10. In fact, the frequency selected for modulation is not critical, and may be selected in accordance with a given implementation. The frequency selected is only limited by practical design constraints of a selected implementation e.g., size of components, processing requirements to implement functions, and the like. The sine wave at frequency f is fed to modulator $m_2$ 54 and to the upper multiplier 230 (e.g., a lock-in amplifier), and the sine wave at frequency 2f is applied only to the lower multiplier 232. A ramp generator 214 similar to that employed in the above embodiments, applies a dc voltage to the $m_1$ modulator 52 to produce the path length bias b, which is adjustable. In an exemplary embodiment, the path length bias b is adjusted to between 0 and $\lambda_o$ to produce a phase shift $\phi_c$ between 0 and $2\pi$. The detected interference signal $i_o$ is amplified and passed through narrow-band filters 210 to produce signals at $\omega$ and at $2\omega$, and these two signals are fed to the multipliers 230 and 232 respectively as shown. The output of the multipliers, after low-pass filtering at 240 and 242, are dc signals which correspond to the parameters in Equations (24) and (25).

It will be readily appreciated that except for the Bessel function coefficients, which are constants whose values are determined by their arguments $2\pi\delta/\lambda_o$, the functions in Equations (24) and (25) are identical to those in Equations (13) and (14) which were obtained from the ramp modulation scheme described earlier. However, advantageously, sinusoidal modulation is more robust and does not need special precautions to generate and control the reference frequency f and the $\pi/2$ electronic phase shift as in the previous case. In an exemplary embodiment the selection of the operating frequency f is arbitrary. However, it is preferable to keep it above the shot noise frequency range, i.e., above 120 KHz, where the shot noise is not significant.

It should also be noted that $\delta$ needs not be large in order to maximize $J_1$. It will be appreciated that the maximum value of $J_1$ $(2\pi\delta/\lambda_o)$ occurs when $(2\pi\delta/\lambda_o)=1.85$, i.e., when $\delta=0.29\lambda_o$, giving $J_1(1.85)=0.582$ and $J_2(1.85)=0.311$. Equations (24) and (25) may then be utilized in a fashion similar to that employed with Equations (13) and (14) in order to measure the phase shift due to the change in index of refraction $\phi_n$ without ambiguity between 0 to $2\pi$.

Similarly, the value of $\Delta n$ may also be obtained from the values in Equations (24) and (25), the known values of $J_1$, $J_2$, and the magnitude of the $I_s$ and $I_r$ (which may be obtained via a calibration), and setting/driving $\phi_c$ to zero. Also as before, in an exemplary embodiment, an implementation employing feedback may be employed to adjust the bias b until the net phase shift is zero. Thereby, the resultant $\Delta n=-b/z$, may readily be obtained. Furthermore, using the value of b to set the frequency of a VCO 150 and zero crossing detector 152, a digital output indicative of the value of b may be obtained to facilitate the computation of $\Delta n$.

It should be further appreciated that the implementation depicted in FIG. 9 includes optional provisions to measure the peak of the interferometric signal $i_o$ under the application of a ramp to provide information on reflection and scattering coefficients. It also contains provision to apply a signal to an optional additional modulator (such as a fiber coil around a PZT drum) to facilitate ranging measurements by means of extra delays applied to the reference arm 42.

In another exemplary embodiment, once the interferometric signal $i_o$ and phase thereof is ascertained, for a selected target depth z, additional LCI interferometric signals $i_o$ corresponding to other target depths may be acquired. Furthermore, if desired, in order to obtain averaged distributions of the LCI signal vs. depth, multiple scans corresponding to multiple target depths may be employed. As disclosed herein, there are several methodologies and exemplary LCI systems that may be employed to acquire an interferometric signal $i_o$ corresponding to selected depths. In one exemplary embodiment, the modulator $m_1$ 52 may be employed to add an additional offsets denoted as $\Delta$ to the reference arm 42 corresponding to a group of target depth variations $\Delta z$ in the vicinity of target depth z. This approach is readily implemented employing the LCI system 10 of FIGS. 4A and 4B. It will be appreciated that the extent of such variations in the target depth $\Delta z$ are a function of the geometry of the waveguide arm and modulators employed. Additional details regarding the waveguide arms 42, and 44 and the configuration of the modulators $m_1$ 52 an $M_2$ 54 are addressed at a later point herein. In addition, an extension module (described at a later point herein) may also be implemented to facilitate variations in target depth and depth scans.

Sensitivity is limited by noise, once the measurement interferometric signal $i_o$ is at or about the noise level it becomes impossible to discern the measurement from noise. Therefore, appreciation of the impact and contributions of noise components becomes instructive with respect to practical considerations of measurement limitations. The detection of the information in Equation (24) is limited by fluctuation noise. The minimum detectable signal is reached when it is equal to the noise, i.e., when the signal-to-noise ratio (SNR) is equal to unity. The noise power is expressed in terms of the photocurrent variance $\sigma_i^2$, which consists of the detector noise $\sigma_r^2$, the photon shot noise $\sigma_s^2$, and for the case of a broadband source 22, the excess photon noise $\sigma_e^2$. Hence, the total noise power is:

$$\sigma_i^2 = \sigma_r^2 + \sigma_s^2 + \sigma_e^2 \qquad (26)$$

The SNR (for signal $I_{o1}$ for example), is given by:

$$SNR = \frac{I_{o1(rms)}^2}{\sigma_i^2}, \text{ where } I_{01(rms)} = \frac{I_{o1}}{\sqrt{2}} \qquad (27)$$

The detector noise power is simply the thermal noise due to the input resistance of the receiver. It is given by $\sigma_r^2=4kTB$, where k is Boltzmann's constant ($k=1.38\times10^{-23}$ J/°K), T is the absolute temperature, and B is the bandwidth of the measurement. For a system having 1 KHz system at room temperature (T=300°K), its value is $1.66\times10^{-17}$ W.

The shot noise, or the noise due to the random arrivals of the photons on the detector 28 from a monochromatic source, obeys Poisson statistics. For a one-ohm resistor, it is given by $\sigma_s^2=2eI_{dc}B$, where e is the electronic charge ($1.6\times10^{-19}$ coulombs) and $I_{dc}$ is the average detector DC current. If the total power incident on the detector 28 is of the order of about 1 mW and the detector quantum efficiency is of the order of unity, then $I_{dc}$ is of the order of 1 mA, and for the same detection bandwidth, the shot noise contribution in a one-ohm input resistor is of the order of about $3.2\times10^{-19}$ W.

The excess intensity noise from a broadband source 22 is a Bose-Einstein process. It is given by (Rollins) $\sigma_e^2=(1+V^2)I_{dc}^2B/\Delta v$, where V is the degree of polarization of the light source 22 and $\Delta v$ its frequency bandwidth. From $v_o\lambda_o=c$, where c is the speed of light in vacuum, the frequency bandwidth is given by $c\Delta\lambda/\lambda_o^2$. For a source 22 with single polarization (V=0), center wavelength of 1.3 µm, FWHM wavelength bandwidth of 60 nm ($\Delta v=1.07\times10^{13}$ Hz) and the same detector current, input resistance and bandwidth as used previously, the excess intensity noise is about $\sigma_e^2=10^{-16}$ W.

All the noise components can be reduced by reducing the electrical bandwidth B. However, it is noteworthy to appreciate that, except at very low total optical power, the excess intensity noise is by far the dominant noise for a broadband source, followed by thermal noise, then the shot noise. Thus, for moderate optical power:

$$SNR \approx \frac{I_{o1(rms)}^2}{\sigma_e^2}, \text{ where } \sigma_e^2 = I_{dc}^2 \frac{B}{\Delta v} \qquad (28)$$

indicating for a broad band source only the excess intensity noise need be considered to evaluate sensitivity. In addition, analysis of the excess intensity noise permits determination of the advantages of employing a phase based techniques of detection/measurement of the interferometric signal $i_o$.

As an example, suppose it is desirable to determine the minimum detectable index change at a depth z in a given specimen with the 1.3-µm light source, 1 KHz detection bandwidth, etc. Assume $I_r \sim 1$ mA, $I_s \sim 0.1$ mA, $J_1=0.582$ and let $\Delta n$ be small enough that the sine term in Equation (24) can be replaced by its argument. Then, for SNR=1, the resultant from Equation (28) yields:

$$(z\Delta n)_{min} \approx 4\times 10^{-6} \text{ µm}. \qquad (29)$$

As mentioned earlier, the minimum detectable index change depends inversely on the probing depth. At a depth of 1 mm, i.e., 1000 mm, the minimum index change is $\Delta n_{(min)} \sim 4 \times 10^{-9}$. At 2 mm probing depth then $\Delta n_{(min)} \sim 2 \times 10^{-9}$. It also depends on the square root of the detection bandwidth, so a factor of three reduction is obtained by reducing the bandwidth from 1 KHz to 100 Hz. The improvement in sensitivity of the phase measurement approach over methodologies employing amplitude stems from the phase factor $\sin(\phi_n)$ in the expression for the phase signal, which does not exist in the amplitude case. At low signal levels, it multiplies the amplitude signal by the factor $2\pi z \Delta n/\lambda_o$ in which the quantity $2\pi z/\lambda_o$ is of the order of 6,000 for the examples used in the calculations.

The interference signal $i_o$ repeats itself after the argument of the sine function in Equation (20) changes by $2\pi$, thus when the coherence length $L_c$ is (larger than about 10 $\lambda_o$) such that the maximum detectable phase change without ambiguity is $2\pi$, equivalent to $\Delta l = \lambda_o$. This yields:

$$(z \Delta n)_{max} = \lambda_o \quad (30)$$

Thus, for example, at a 1.3-μm wavelength, $\Delta n^{(max)} \sim 1.3 \times 10^{-3}$ at 1-mm probing depth, and $\Delta n_{(max)} \sim 6.5 \times 10^{-4}$ at 2-mm probing depth. Just as the probing depth can be used to control the sensitivity, it can also be used to control the maximum detectable change. The range of the instrument is the ratio of the maximum to minimum detectable signals. For the examples discussed herein, this range is $3 \times 10^5$ or 55 dB. For a larger index change, methodology that may be employed is to use the envelope detection method or a combination of phase and envelope detections as described earlier. Note that, since these results are independent of the overall magnitude of the interferometric signal, it is sufficient to make these measurements at only one depth. The depth needs to be changed only to change the scale of the LCI system 10.

It is well known that the refractive index change $\Delta n$ in the dermis due to the presence of glucose is $\sim 1.52 \times 10^{-6}$ per milligram per deciliter (mg/dl). Therefore, by establishing variation in the index of refraction, a glucose determination may be determined. In an exemplary embodiment, a comparison of current measurements for index of refraction and a baseline measurement based on calibration and/or normalization for a particular patient yields an accurate means of determining the current glucose concentration.

Assuming a linear dependence, this gives a glucose concentration C of $$C = 6.58 \times 10^5 \Delta n \text{ mg/dl} \quad (31)$$

With the numbers given above, it will be appreciated that glucose levels from about 0.0026 mg/dl to about 855 mg/dl can be measured at 1-mm probing depth. Similarly, glucose levels from about 0.0013 mg/dl to about 428 mg/dl at 2-mm probing depth. The acceptable glucose concentration in humans ranges from about 70 mg/dl to about 170 mg/dl. Therefore, it is evident that the methodologies disclosed provide a significant benefit when applied particularly to glucose monitoring.

Correlations of glucose concentrations between LCI-based non-invasive measurements employing such methodologies and invasive measurements in the range of about 80–95% can be achieved. It will further be appreciated that when compared to other analytes, glucose, sodium chloride (NaCl), potassium chloride (KCl), and urea produced the highest changes in ISF refractive index with glucose exhibiting the most pronounced effect.

Referring once again to FIGS. 4A and 4B, broadband light sources including, but not limited to, SLD's are laser type structures configured and designed to operate substantially without feedback, e.g., of the order of less than $10^{-3}$, preferably less than $10^{-4}$, more preferably less than $10^{-5}$. In the presence of feedback, the spectrum of the SLD light source 22 may be distorted, the coherence is significantly increased and the spectrum can exhibit very large ripples and even lasing spikes, and thereby may become lasers. Therefore, to prevent distortion and maintain spectral integrity, low coherence, and broadband characteristics, reflections back into the light source 22 are avoided to maintain a broadband light source 22. Thus, in an exemplary embodiment of the LCI system, isolation is provided to alleviate feedback to the light source 22.

Continuing with FIGS. 4A and 4B, in an exemplary embodiment, the source-detector module 20a, 20b, is configured to prevent the reflected interferometer light from reaching the SLD light source 22 and upsetting its operation. The SLD source 22 is designed and configured such that it is linearly-polarized. SLDs and lasers are "heterostructures" semiconductor devices consisting of a thin "active" layer sandwiched between two "cladding" layers of lower refractive index, all epitaxially grown on a single crystal substrate 23. One such process for fabrication is known as MOCVD (metalorganic chemical vapor deposition). One of the cladding layers is p-doped, and the other is n-doped. The substrate 23 is typically n-doped, and the n-cladding layer is the first to be deposited on it. The structure forms a p-n semiconductor junction diode, in which the active layer is caused to emit light of energy equal to its bandgap upon the application of an electric current.

The structure is called heterostructure because the active and clad layers are made of different material. This is in contrast with ordinary diodes in which the p-n junction is formulated between similar materials of opposite doping. The use of heterostructure has made it possible to confine the electrical carriers to within the active region, thus providing high efficiency and enabling operation at room temperature. In many heterostructures, light is emitted in both TE polarization (the electric field in the plane of the layer) and TM polarization (electric field perpendicular to the layer).

However, useful effects are obtained when the active layer is sufficiently thin such that quantum mechanical effects become manifest. Such thin layers are called "quantum well" (QW) layers. Furthermore, the active layer can be "strained", i.e., a slight mismatch (of about 1%) with respect to the substrate crystal lattice can be introduced during the deposition of the QW layer. The strain can modify the transition characteristics responsible for light emission in beneficial ways. In particular, the light is completely polarized in the TE mode if the strain is compressive. Thus, it is now possible to make a linear polarized laser or broadband SLD by compressive strain of the active layer. In an exemplary embodiment, such a linearly-polarized light source 22 is employed.

In one exemplary embodiment, as depicted in FIG. 4A, the light from the light source 22 is directed through an isolator 24 configured to transmit light in one direction, while blocking light in the opposite direction. The light is directed to a splitter/coupler 50 of the splitter-modulator module 40a. The source-detector module 20a also contains a detector 28 to receive from the splitter/coupler 50.

In another exemplary embodiment as depicted in FIG. 4B, the linearly-polarized light from the SLD light source 22 is collimated with lenses 27 and applied to a splitter 25. If a basic 50/50 splitter 24 is employed, half of the returned light goes to the detector 28 and the other half is directed to the SLD light source 22. Once again, in this configuration an isolator 24 may be employed to prevent feedback to the light source 22. Similarly, as stated earlier, in another exemplary embodiment, the splitter 25 is a polarizing beam splitter 25 operating in cooperation with a quarter wave plate 26, employed to prevent feedback light from reaching the light source 22. The polarizing beam splitter 25 facilitates the elimination of feedback to the SLD light source 22 by redirecting substantially all the reflected light from the splitter-modulator module 40b to the detector 28.

The splitter 25 transmits the horizontally polarized light to the quarter wave plate 26, which coverts the light to another polarization, (for example, circular polarization). Likewise, the returning, circularly polarized light is received by the quarter wave plate 26 and is reconverted to a linear polarization. However, the linear polarization opposite, for example, vertical. The vertically polarized light is transmitted to the polarizing beam splitter 25, which directs all of the light to the detector 28. Advantageously, this approach transmits substantially all of the light i.e., the interference signal, to the detector 28. Whereas embodiments employing the isolator 24 transmits approximately half of the light to the detector 28.

The polarizing beam splitter 25 is a device that transmits light of one polarization (say the horizontal, or TE-polarized SLD light) and reflects at 90° any light of the other polarization (e.g., vertical or TM-polarized). The quarter-wave plate 26 is a device that converts a linearly polarized incident light to circular polarization and converts the reflected circularly-polarized light to a linearly-polarized of the other polarization which is then reflected at a 90° angle by the polarizing beam splitter 25 to the detector 28. Therefore, essentially all the light transmitted by the light source 22 is re-polarized and transmitted to the splitter-modulator module 40b and all the reflected light from the sample and reflecting device 48 is deflected by the polarizing beam splitter 25 to the detector 28. Advantageously, this doubles the light received at the detector 28 relative to the other embodiments, and at the same time minimizes feedback to the SLD light source 22.

In an exemplary embodiment an SLD chip for the light source 22 has dimensions of approximately 1 mm×0.5 mm×0.1 mm (length×width×thickness), and emits a broadband light typically of up to 50 mW upon the application of an electric current of the order of 200–300 mA. The light is TE-polarized if the active layer is a compressively strained QW. The FWHM spectrum is of the order of 2% to 3% of the central wavelength emission. A SLD light source 22 with 1.3 μm center wavelength emission and operating at 10 mW output power at room temperature would have a bandwidth of about 40 nm and would require about 200 mA of current. In an exemplary embodiment, for continuous wave (cw) operation at room temperature, the SLD light source 22 may be mounted on an optional thermoelectric cooler (TEC) 32 a few millimeters larger than the SLD light source 22 chip to maintain the temperature of the light source 22 within its specified limits. It will be appreciated that the SLD light source 22 and associated TEC 32 peripherals in continuous operation would have the largest power consumption in the LCI system 10. However, without the TEC 32, the SLD junction temperature would rise by several degrees under the applied current and would operate at reduced efficiency.

Advantageously, in yet another exemplary embodiment, the utilization of a TEC 70 may readily be avoided without incurring the effects of significant temperature rise by pulsed operation of the SLD light source 22. Pulsed operation has the further advantage of reducing the SLD electrical power requirement by a factor equal to the pulsing duty cycle. Moreover, for selected applications of digital technology and storage, only a single pulse is sufficient to generate an interference signal and retrieve the desired information. Therefore, for example, with pulses of duration 10 μs and 1% duty factor, the LCI system 10 of an exemplary embodiment can average 1000 measurements per second without causing the SLD light source 22 temperature to rise significantly. Thus, for low power consumption, the LCI system 10 should preferably be designed for the SLD light source 22 to operate in a pulsed mode with a low duty cycle and without a TEC 32. In such a configuration the source-detector module 20 would be on the order of about 2 centimeters (cm)×2 cm×1 cm.

The splitter-modulator module 40a, and 40b of an exemplary embodiment includes a splitter/coupler 50 and Y-splitter/combiner 51 respectively, with a "reference" arm 42 and a "sensing" arm 44, the reference arm 42 having a slightly longer optical path (for example, 1 to 3 mm for measurements in biological tissues) than the sensing arm 44. The optical path difference between the two arms 42, 44 is configured such that the LCI system 10 balanced for the chosen probing depth z. Provision is also made to include a modulator $m_1$ 52 and $m_2$ 54 in the reference arm 42 and sensing arm 44 respectively.

In an exemplary embodiment, the splitter/coupler 50, Y-splitter/combiner 51 reference arm 42 and a sensing arm 44 are formed as waveguides in a substrate. However, other configurations are possible, including but not limited to separate components, waveguides, optical fiber, and the like. The substrate 23 for this module should preferably, but not necessarily, be selected such that the waveguides of the arms 42, 44 and modulators 52, 54 can be fabricated on/in it by standard lithographic and evaporation techniques. In one exemplary embodiment, the waveguides of the arms 42, 44 are fabricated by thermal diffusion of titanium or other suitable metal that increases the index of refraction of the substrate, evaporated through masks of appropriate width for single transverse-mode operation. In another exemplary embodiment, the waveguides are formed by annealed proton exchange in an acid bath. This process raises the refractive index in the diffusion region, thus creating a waveguide by virtue of the refractive index contrast between the diffusion region and the surrounding regions. In an exemplary embodiment, is lithium niobate (LiNbO3) is employed as a substrate 23. It will be appreciated that other possible materials, namely ferroelectric crystals, may be utilized such as lithium tantalite (LiTaO3) and possibly indium phosphide depending on configuration and implementation of the LCI system 10.

Lithium niobate is a ferroelectric crystal material with excellent optical transmission characteristics over a broad wavelength range from the visible to the infrared. It also has a high electro-optic coefficient, i.e., it exhibits a change of refractive index under the application of an external electric field. The refractive index change is proportional to the electric field. The speed of light in a transparent solid is slower than in vacuum because of its refractive index. When light propagates in a waveguide built into the electro-optic material, an applied electric field can alter the delay in the material, and if the electric field is time-varying, this will result in a phase modulation of the light. The LiNbO3 material is very stable, the technology for making it is mature, and LiNbO3 modulators, which can be compact and are commercially available.

In an exemplary embodiment, the high electro-optic coefficient (refractive index change with applied electric field) of lithium niobate is exploited to facilitate implementation of a modulator, such as modulators $m_1$ 52 and $m_2$ 54. In this embodiment, a modulator is implemented on or about the waveguide arms 42, 44, by depositing metal electrodes 56, 58 in close proximity to the waveguide arms. In one embodiment, the metal electrodes 56, 58 are deposited on the sides of the waveguide arms 42, 44. In another, the metal electrodes 56, 58 may be deposited on the waveguide arms 42, 44 with an appropriate insulation layer, in a selected region. FIGS. 4A and 4B also shows a diagrammatic depiction of a modulators $m_1$ 52, $m_2$ 54 in each arm 42, 44 fabricated by depositing metal films (electrodes) 56 on the outside the waveguides and a larger "common" electrode 58 between them. Modulation with modulator $m_1$ 52 is obtained by applying a voltage between the upper electrode 56 and the common electrode 58, and modulation with modulator $m_2$ 54 is obtained by applying a voltage between the lower 56 and the common electrodes 58. The change of refractive index with applied voltage results in a delay or a change of optical path between for the modulated arm 52, 54. For a given applied voltage, the optical path change depends on the length of the electrodes 56, 58.

Figure 14:
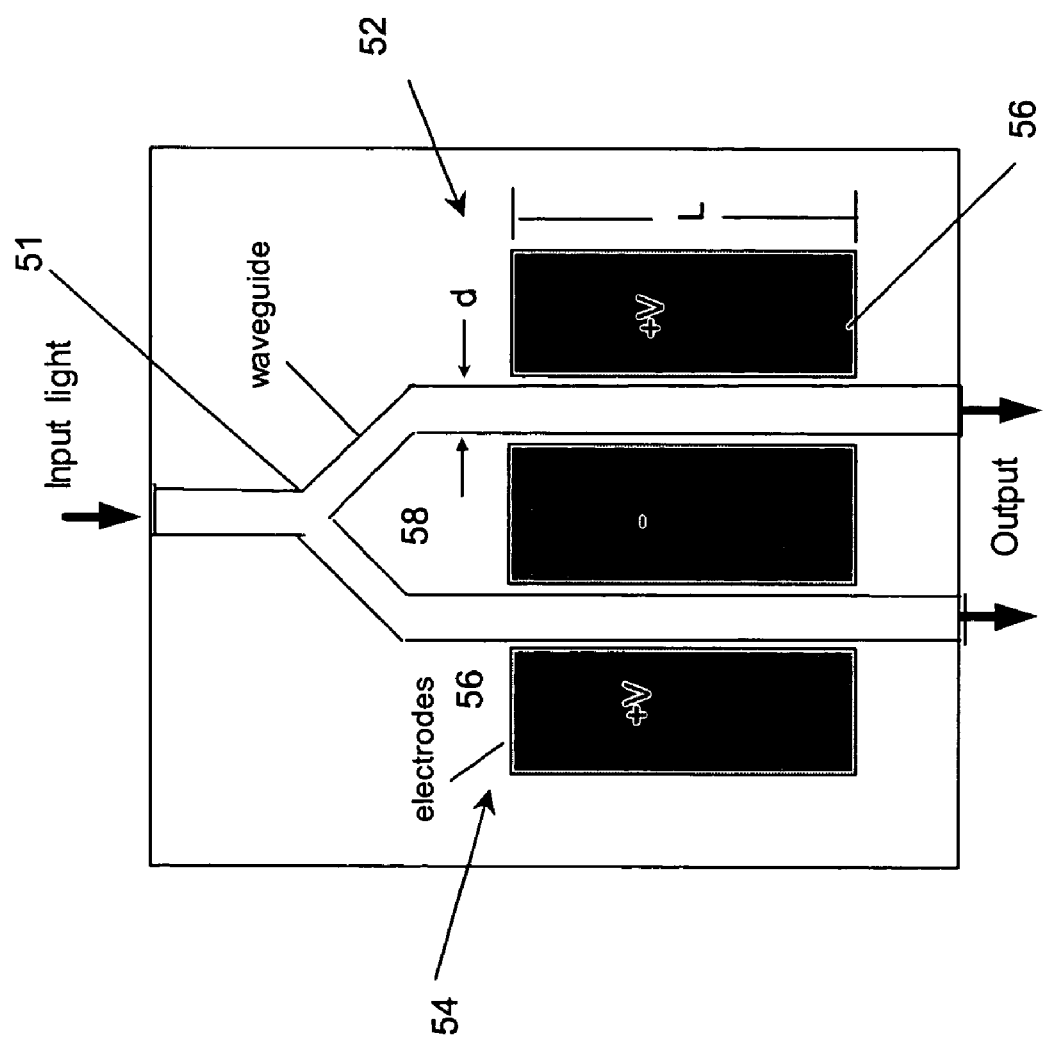
FIG. 14 depicts an illustration of a splitter-modulator module in accordance with an exemplary embodiment.

FIG. 14 depicts an illustration of a splitter-modulator module 40b with a Y-splitter 51 and two modulators 52, 54 integrated on a LiNbO3 substrate 23. One method of making the Y-splitter 51 (or splitter/combiner 50 of splitter-modulator module 40a) and waveguide arms 42, 44 is by diffusing titanium or another suitable metal into a substrate 23 at high temperature. Another method of fabrication is by proton exchange in an acid bath. In an exemplary embodiment, titanium and a lithium niobate substrate 23 are employed. The process of fabricating the module 40b (or 40a) is illustrated in FIGS. 15A–C. In the diffusion process, the waveguide pattern is etched in a mask and a thin layer of titanium is vacuum-deposited onto the substrate 23 through the mask. The substrate 23 is then heated in an oven at about 900–1000 degrees C. to diffuse the titanium into the lithium niobate substrate 23. The index of refraction of the diffusion region is slightly higher than that of the surrounding material, and this constitutes waveguides in which light is guided in the diffusion region by virtue of its higher refractive index (just as in an optical fiber where the light propagates in the higher index core). Following diffusion, the metal electrodes 56 and 58 for the modulator(s) 52, 54 are deposited on the sides as shown, with a small spacing d between them. Application of a voltage V between one of the outer electrodes 56 and the negative center electrode 58 establishes an electric field of value V/d across the waveguide e.g. reference arm 42 and/or sensing arm 44. In an exemplary embodiment, the width of the waveguide is approximately 3–5 microns, and the spacing d is only a few more microns wider.

The refractive index change due to the electro-optic effect is given by $$\Delta n = -\frac{1}{2} n_o^3 r \frac{V}{d} \tag{32}$$

where $n_o$ is the refractive index, and r is the electro-optic coefficient. The phase shift of a light of wavelength $\lambda$ propagating in a LiNbO3 modulator is given by $$\Delta \phi = \pi \frac{L}{\lambda} n_o^3 r \frac{V}{d} \tag{33}$$

where L is the length of the modulator electrodes 56, 58. In the context of the LCI systems 10 disclosed herein, this corresponds to an optical path length change of $$\Delta l = \frac{1}{2} n_o^3 r L \frac{V}{d} \tag{34}$$

Typical material properties are:

$r = 11.3 \times 10^{-12}$ m/V $n_o = 2.35$

To obtain larger scale modulations, it will be appreciated that an increase in the voltage on/or the length of the modulator will result in larger changes in the index of refraction by the modulator, resulting in an increased variation of the corresponding phase delay. For example, with a configuration of d=10 microns, an applied voltage of only 3.6 volts is sufficient to yield a value of $\Delta l$ or b (as discussed above) of 1.3 microns (the wavelength of the light discussed in the examples above). This illustrates that a modulator with a range equivalent to the wavelength $\lambda$ (for example) 1.3 microns may readily be achieved employing the configuration described.

In an exemplary embodiment, the reference arm 42 is terminated in an evaporated mirror (metal or quarter-wave stack) 46, and the sensing arm 44 is terminated in an anti-reflection (AR) coating, or is covered with an index-matching agent 48 that prevents or minimizes reflection from the end of the sensing arm 44 when placed in contact with the object to be measured. In such a configuration splitter-modulator module 40 would be on the order of about 2 cm×2 cm×0.5 cm.

Figure 16:
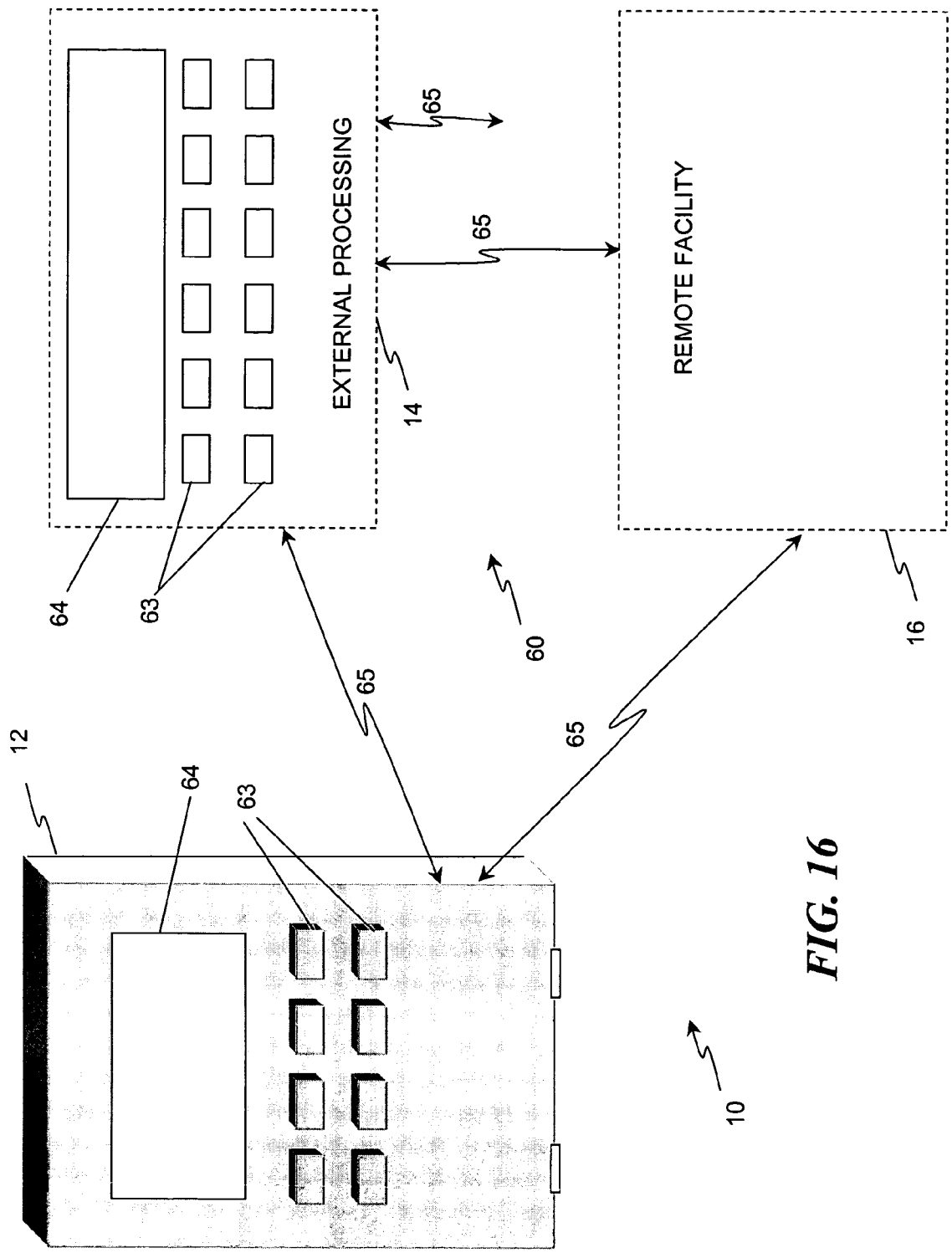
FIG. 16 depicts a miniaturized, handheld LCI system in accordance with an exemplary embodiment.

Referring now to FIG. 16, a miniaturized, optionally handheld, LCI system 10 is depicted in accordance with an exemplary embodiment. In an exemplary embodiment, the LCI system 10 is packaged in a small enclosure 12 and includes, but is not limited to, various modules including, but not limited to source-detector module 20a, 20b, splitter-modulator module 40a, 40b and may include one or more additional extension, adapter or interface modules such as 80, 90, and 92 (See FIGS. 4A, 4B and 10–13) or even calibration strip 70. In addition, also optionally packaged within the enclosure may be processing system 60, including processor 62 (not shown in this view) associated controls 63 e.g., keys, selectors, pointers, and the like, display 64, data media 66, as well as communication interfaces 65, and the like as well as rechargeable batteries. Therefore, in one exemplary embodiment the LCI system 10 as packaged in enclosure 12 should be comparable in size to that of a typical cell phone or a Personal Digital Assistant (PDA), i.e., about 4 cm×6 cm×1 cm. to readily facilitate handheld operation.

Continuing with FIG. 16, it should also be appreciated as mentioned earlier, that various portions of the LCI system 10, and particularly, processing system 60 may be enclosed within the enclosure 12, or associated with an external processing unit 14, or remotely located, such as with a computer processing system 60 in another facility 16. In yet another exemplary embodiment, the LCI system 10 may also include communication interfaces 65, including wireless interfaces (e.g., infrared, radio frequency, or microwave transmitter/receiver) similar to modern computers, cell phones, PDAs, and the like to enable communication, including, but not limited to Internet communication, with external systems 14 and remote facilities 16. For example, as a non-invasive glucose monitor and controller, a sensing portion including the source-detector module 20a, 20b and splitter-modulator module 40a, 40b can be detachable, in the form of a wrist band or wrist watch for continuous monitoring, while the rest of the remainder of the LCI system 10 may be in a patient's pocket, separate computer, at a doctor's office, and the like.

Figure 17A:
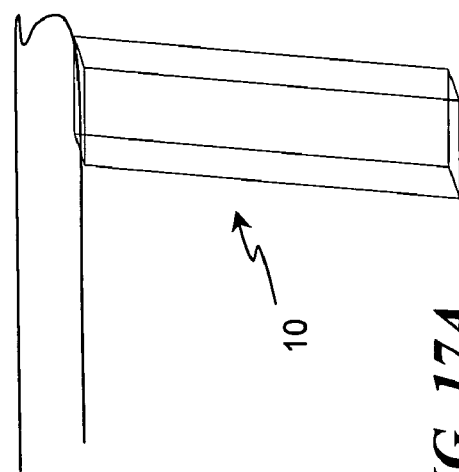
FIG. 17A depicts operation of a miniaturized, handheld LCI system in accordance with an exemplary embodiment.
Figure 17B:
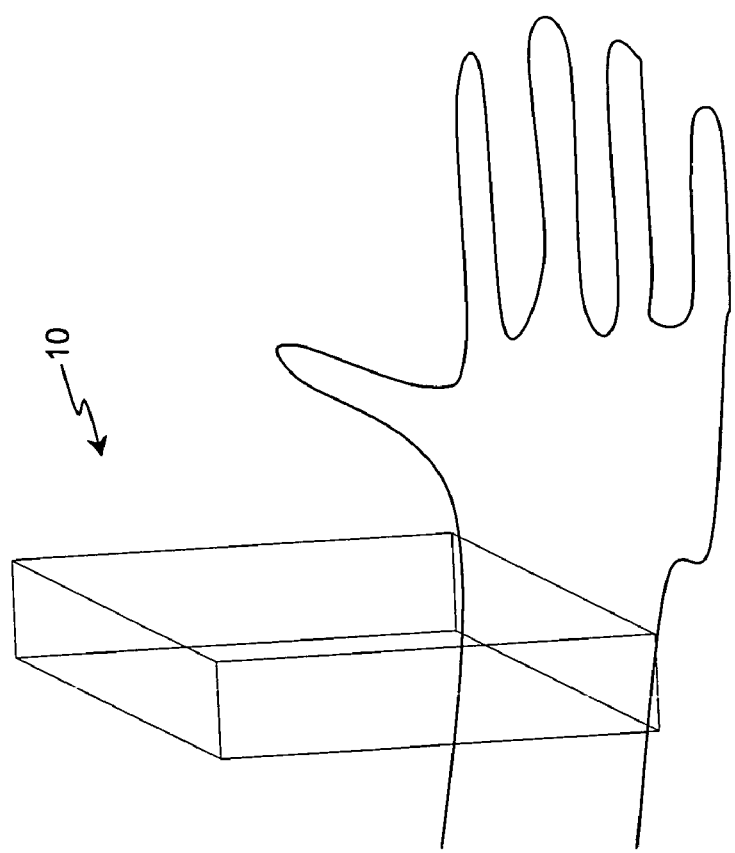
FIG. 17B depicts operation of a miniaturized, handheld LCI system in accordance with another exemplary embodiment.

Referring now to FIGS. 17A and B, to illustrate operation of the LCI system 10, as a non-invasive glucose monitor, the instrument is placed against the skin at some location such as the finger, the back of the hand, or the arm. It should be noted that the finger presents a desirable location for sensing, since it has no hair and few other features that may interfere with the light path. However, other locations are possible. The LCI system 10 would rapidly measure and determine the glucose concentration, (or a multitude of measurements can be made and averaged over a few seconds). A display 66 may also be utilized to provide visual information with respect to measurement to a patient. Furthermore, the LCI system 10 could be coupled to a dispenser embedded in the patient for real-time control and administration of medications such as, insulin.

Figure 10:
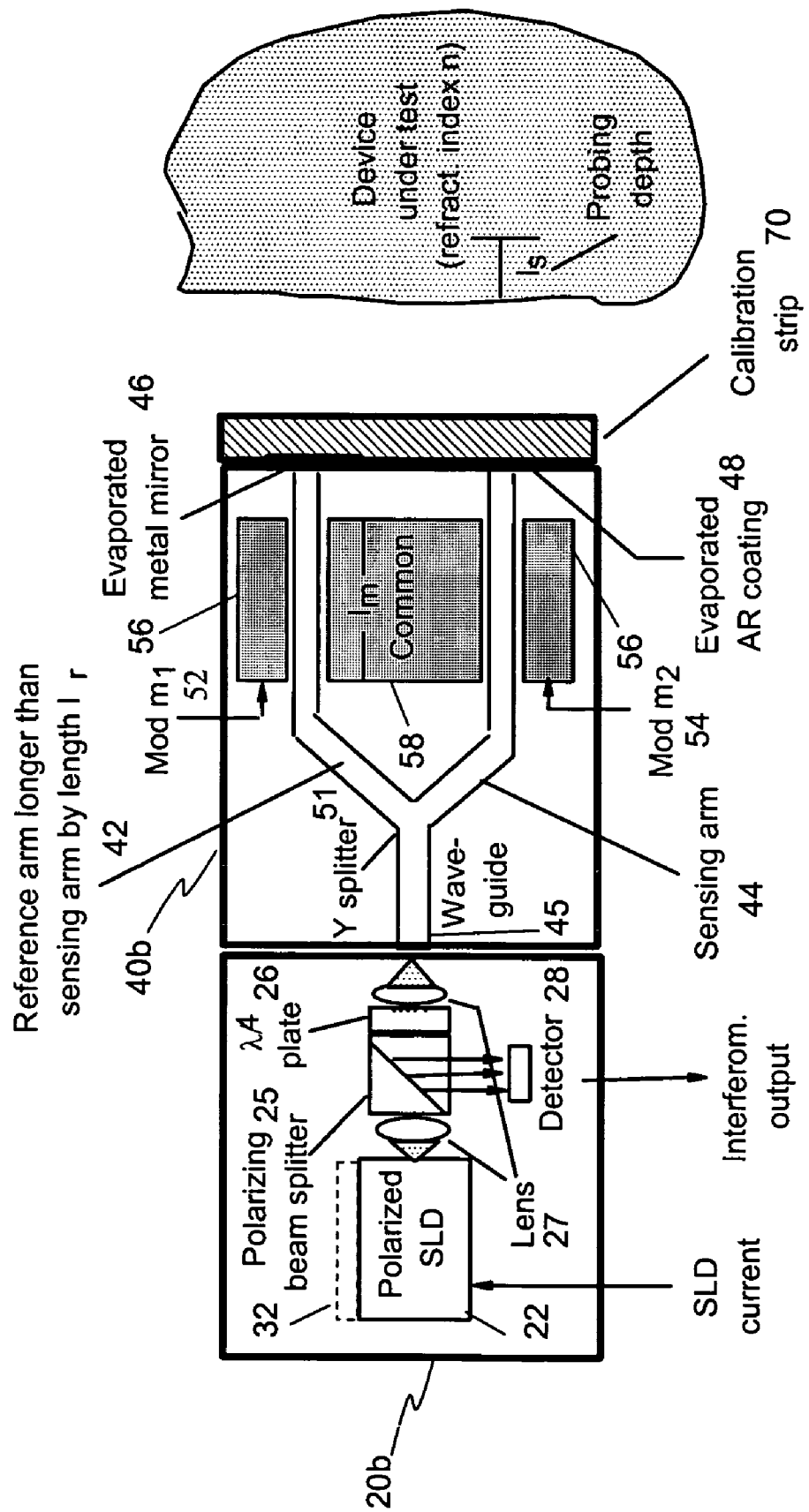
FIG. 10 depicts an adaptation of the interferometer system of FIGS. 4A and 4B with a calibration strip.
Figure 11:
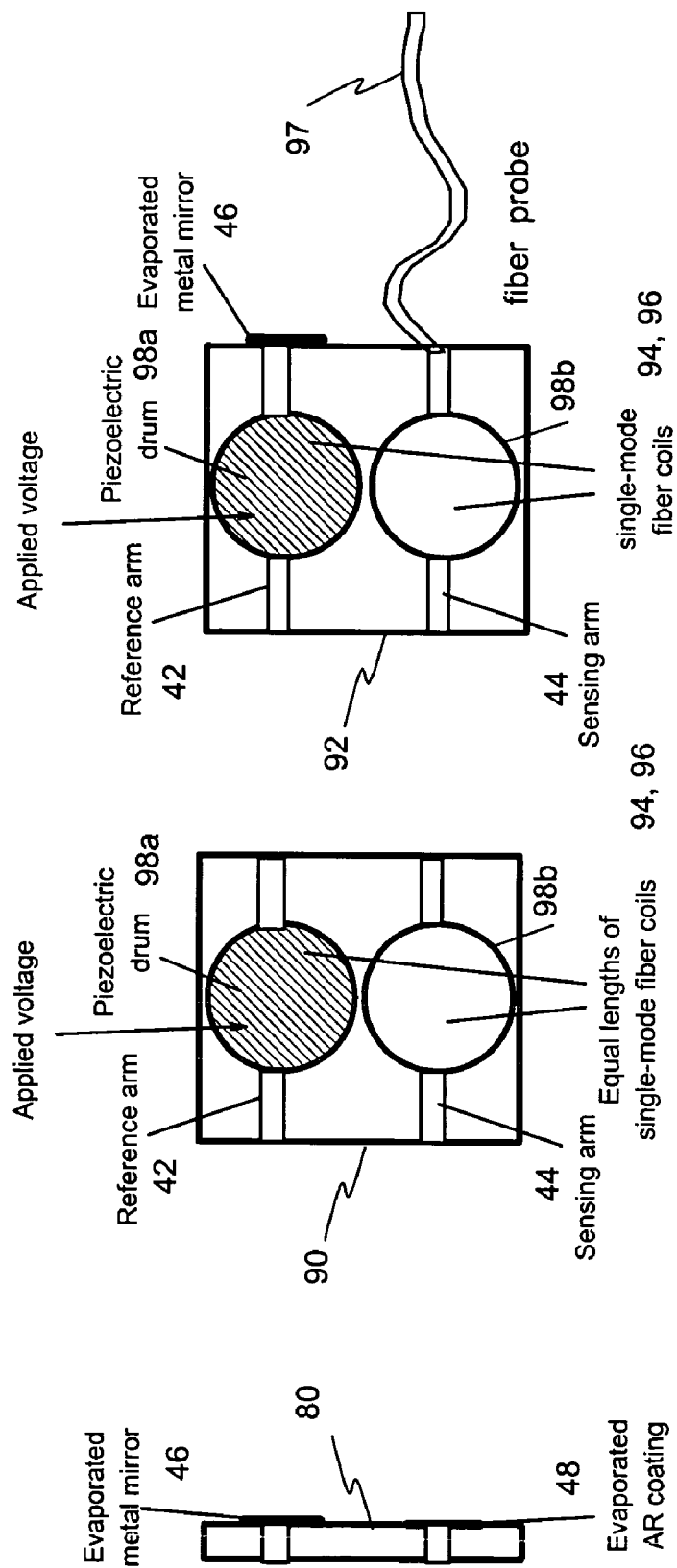
FIG. 11A depicts an interface for extension modules in accordance with another exemplary embodiment of the invention.
FIG. 11B depicts an interface for extension in accordance with another exemplary embodiment of the invention.
FIG. 11C depicts another interface for extension in accordance with yet another exemplary embodiment of the invention.

The phase associated with a selected length of the reference arm is pre-calibrated to correspond to a set distance (about 1 to 3 mm) under the skin. The spot size for the light at the tip of the sensing fiber or waveguide of the sensing arm 44 is on the order of a few microns. The LCI system 10 may readily be calibrated by placing a strip of known refractive index (or, in the case of a glucose monitor, known glucose content,) and appropriate thickness at the sensing end of the splitter-modulator module 40 prior to performing a measurement. FIG. 10 depicts the LCI system of FIGS. 4A and 4B with a calibration strip in place. The calibration strip 70 can serve the dual purpose of calibration and refractive index matching. Its placement in contact with the splitter-modulator module 40a, 40b does not affect the reference arm 42, since the reference arm light does not penetrate it due to the presence of the end mirror 46. The calibration strip 70 and associated processing may be configured such that the LCI system 10 provides a first reading when the calibration strip 70 is not in contact with the LCI system 10 and a corrected reading when in contact with the calibration strip. Furthermore, the calibration strip may be configured as a disposable item.

The configuration described above with reference to FIGS. 4A and 4B is convenient to use when the instrument can be placed directly in contact with the sample to provide a reading for a selected depth. Some applications may require the probing depth to be dynamic to enable locating a feature. For example, in medical diagnostics or imaging, the operator may need to probe for features such as tumors, characterized by large changes of optical properties (absorption, reflection, or refractive index change due to a different density). Some other (medical) applications may require a probe to be inserted into the body or object under study. For example, employing an expansion to the embodiments disclosed herein with a fiber probe with a catheter and guide wire to facilitate internal diagnostics and imaging. FIGS. 11A–11C depict an adapter and several expansion or extension modules 90, 92, which can be attached to the LCI system 10 of FIGS. 4A and 4B to provide additional versatility and functionality. FIG. 11A, depicts an adapter 80, configured, in one exemplary embodiment as a short section of waveguides 82, preferably, but not necessarily, made of the same material as the splitter-modulator 40a, 40b, with mirror 46 and AR coating 48, which can be attached to the splitter-modulator 40a, 40b (with matching fluid) to operate as an interface for various extension modules 90, 92. The purpose of the extension module 90 is to provide for adequate lengths of the reference and sensing arms 42, 44 while using a minimum of space, and for adjusting the length of the reference arm 42 and/or sensing arm 44 to enable probing at various depths. The length of the arms 42, 44 can be adjusted in any number of ways, including mechanically changing an air gap between two sections of the reference arm, moving the mirror 46, actually modifying the length of the arm, and the like, as well as combinations including at least one of the foregoing. A preferred way to manipulate the length of an arm 42, 44, in this instance the reference arm 42, in order to maintain small size, accuracy, and stability, is to perform this operation electromechanically.

Referring now to FIGS. 11B and 11C, in yet another exemplary embodiment, an extension modules 90 and 92 including windings of two lengths of single-mode fibers 94, 96, preferably a polarization maintaining fiber (PMF), (reference and sensing arms respectively) on two drums 98a and 98b. In one embodiment, the drum for the reference arm 42 is made out of a piezoelectric material such as, but not limited to PZT (lead zirconate titanate). The diameter of the drums is selected to be large enough to prevent radiation from the fibers 94, 96 due to the bending for example, about 3–4 centimeters (cm). The diameter of the fibers 94, 96 with claddings is of the order of 0.12 mm. The application of a voltage to the PZT drum 98a causes it to expand or contract, thus straining the reference fiber 94 (for example) and changing its effective length and thereby the optical path length for the reference arm 42. Therefore, as the total length of the unstrained fiber is increased, the total expansion increases as well. For example, if the strain limit for the fiber 94 is about $\Delta l/l$ is $10^{-4}$, then it requires a 10-meter length of fiber 94 to provide for about a 1 mm extension. Advantageously, a length tens of meters is relatively easy to achieve if the fiber 94 is not too lossy. In the 1.3 μm to 1.55 μm wavelength range, the absorption in optical fibers 94, 96 is of the order of 0.2 dB/Km. There for the losses associated with a 10 meter length would be quite small. Thus, the approach of using a voltage applied a piezoelectric drum e.g., 98a wound with a fiber 94 coil is an effective means to provide changes of several millimeters in the optical path length of the reference arm 42.

Continuing with FIGS. 11B and 11C, the extension module 90 is configured to provide the extension of the reference and sensing arms 42 and 44 as described above and interfaces with an adapter 80 to facilitate depth profiling. Extension module 92 also includes an evaporated metal mirror 46 to terminate the reference arm 42, while the sensing arm 44 is terminated with a fiber probe 97 configured to facilitate probing such as may include a guidewire and catheter.

Figure 12:
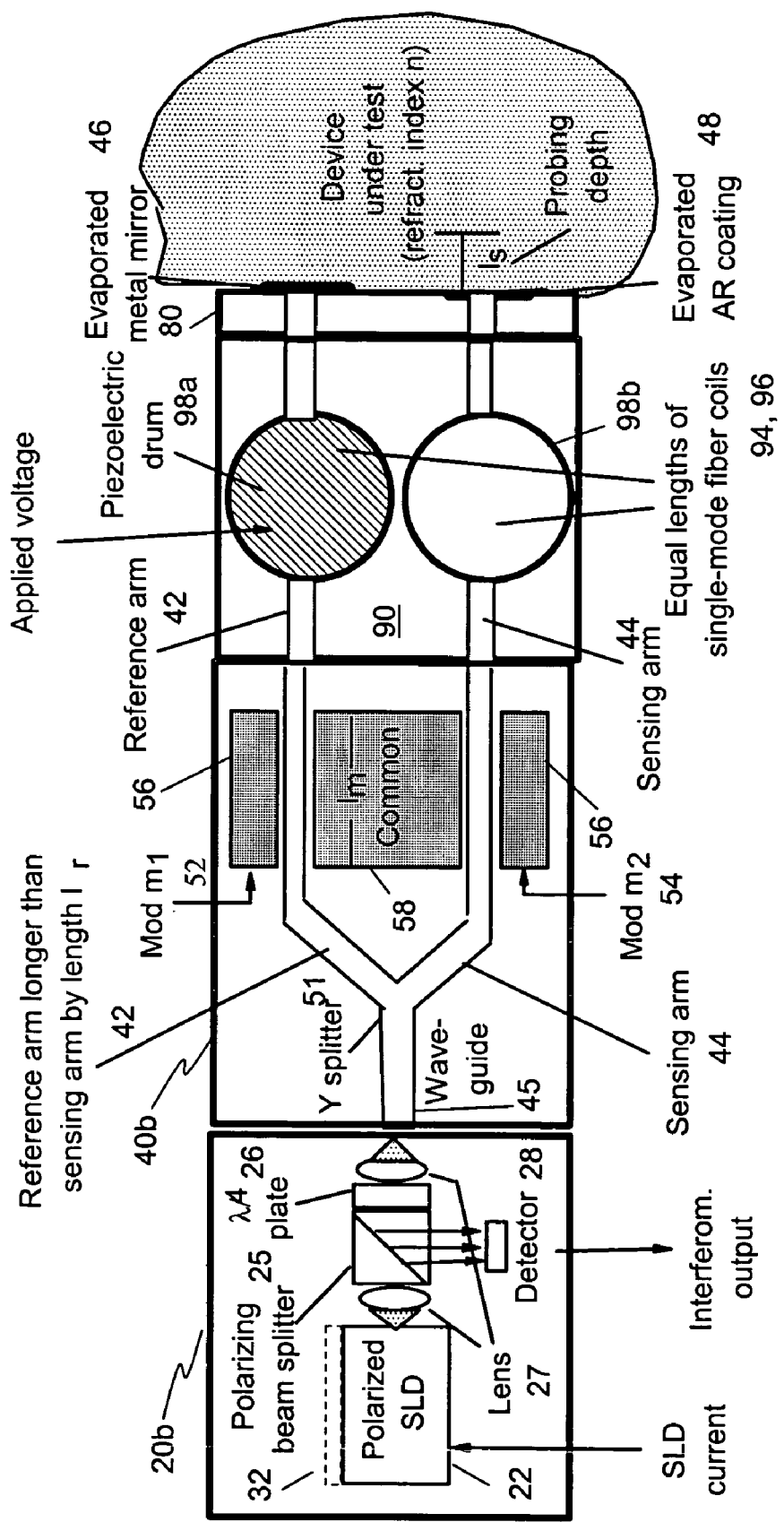
FIG. 12 depicts an adaptation of the interferometer system of FIGS. 4A and 4B for ranging measurements in accordance with another exemplary embodiment.
Figure 13:
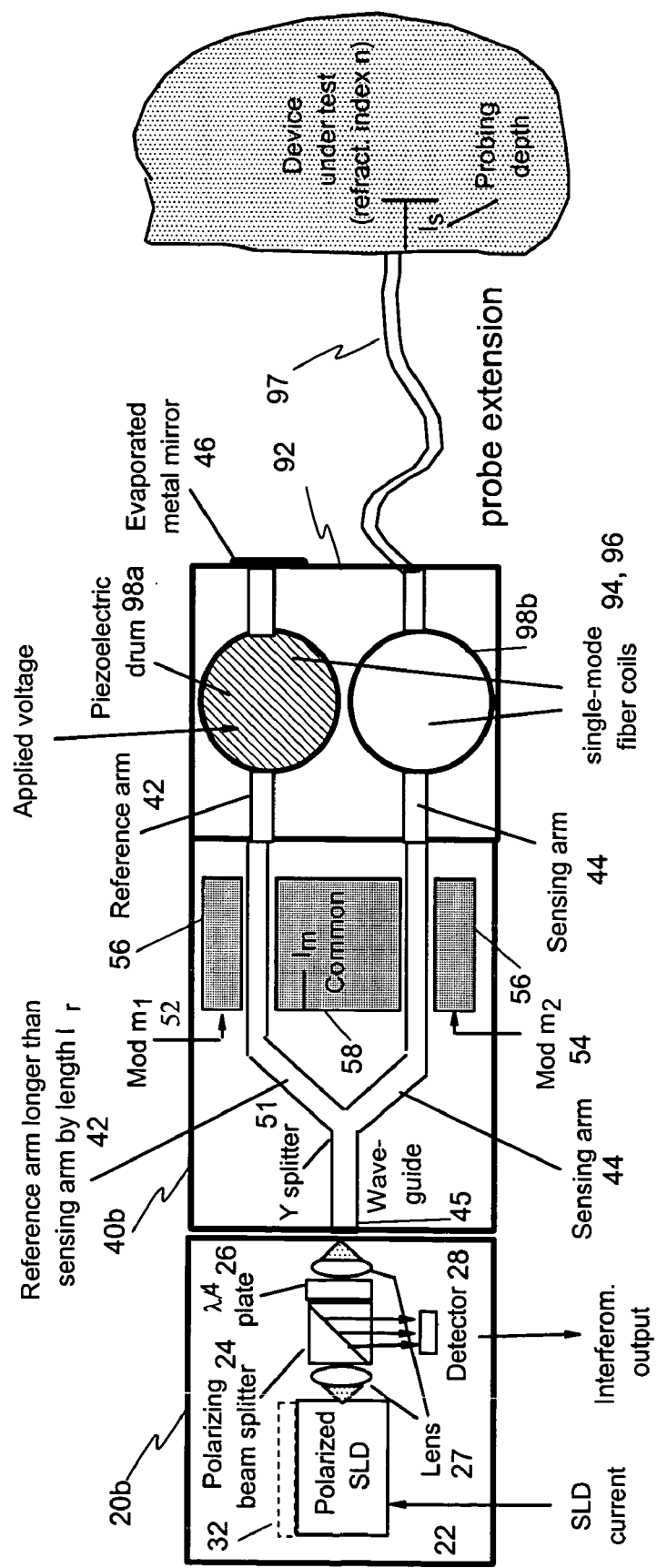
FIG. 13 depicts another adaptation of the interferometer system of FIGS. 4A and 4B for ranging measurements in accordance with yet another exemplary embodiment with external probe.

FIGS. 12 and 13 depict various implementations of the extended instrument starting from the base configuration depicted in FIGS. 4A and 4B and using the adapter and the extension modules 80, 90, and 92. FIG. 12 depicts a configuration of an exemplary embodiment where in addition to the source-detector module 20a, 20b and splitter modulator module 40a, 40b and extension module 90 and adapter 80 are employed. This configuration facilitates probing at various depths as well as facilitating depth profile scanning. FIG. 13 depicts a configuration of another exemplary embodiment where in addition to the source-detector module 20 and splitter modulator module 40 and extension module 92 including an external probe 97 are employed. This configuration facilitates probing either at a distance from the device or remote probing such as with a catheter and guidewire. FIG. 12 depicts a configuration of an exemplary embodiment where in addition to the source-detector module and splitter modulator module 40a, 40b and extension module 90 and adapter 80 are employed. This configuration facilitates probing at various depths as well as facilitating depth profile scanning.

The disclosed invention can be embodied in the form of computer, controller, or processor implemented processes and apparatuses for practicing those processes. The present invention can also be embodied in the form of computer program code containing instructions embodied in tangible media 66 such as floppy diskettes, CD-ROMs, hard drives, memory chips, or any other computer-readable storage medium, wherein, when the computer program code is loaded into and executed by a computer, controller, or processor 62, the computer, controller, or processor 62 becomes an apparatus for practicing the invention. The present invention may also be embodied in the form of computer program code as a data signal 68 for example, whether stored in a storage medium, loaded into and/or executed by a computer, controller, or processor 62 or transmitted over some transmission medium, such as over electrical wiring or cabling, through fiber optics, or via electromagnetic radiation, wherein, when the computer program code is loaded into and executed by a computer 62, the computer 62 becomes an apparatus for practicing the invention. When implemented on a general-purpose processor the computer program code segments configure the processor to create specific logic circuits.

It will be appreciated that the use of first and second or other similar nomenclature for denoting similar items is not intended to specify or imply any particular order unless otherwise stated.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for diagnosing a human condition from a characteristic of an analyte in a biological sample, the method comprising:
   directing broadband light by means of a sensing light path at the biological sample, at a target depth defined by said sensing light path and a reference light path;
   receiving said broadband light reflected from the biological sample by means of said sensing light path;
   directing said broadband light by means of said reference light path at a reflecting device;
   receiving said broadband light reflected from said reflecting device by means of said reference light path;
   modulating at about a distance of a center wavelength of said broadband light an effective light path length of at least one of said reference light path and said sensing light path with respect to said target depth;
   detecting said broadband light resulting from said broadband light reflected from said target depth in the biological sample and said broadband light reflected from said reflecting device, to generate a signal indicative of an interference of said broadband light reflected from said target depth in the biological sample and said broadband light reflected from said reflecting device, wherein said signal is a product of a cosine function;
   determining a phase component that is an argument of the cosine function;
   determining a change in the phase component angle of said signal resulting from a change of said effective light path length that is itself induced by a change of a property of the biological sample;
   determining a variation in an index of refraction from said change in the phase component of said signal;
   determining the characteristic of the analyte in the biological sample from said variation in said index of refraction; and
   diagnosing a human condition from the characteristic.

2. The method of claim 1 further comprising varying an effective light path length of at least one of said reference light path and said sensing light path to define an other target depth, said other target depth is at a distance of about at least a coherence length of broadband light from said target depth.

3. The method of claim 2 wherein said varying an effective light path length of at least one of said reference light path and said sensing light path employs at least one of a modulator comprising metallic electrodes disposed at an optical waveguide and a modulator formed with an optical fiber wound on a piezoelectric drum forming at least a portion of at least one of said reference light path and said sensing light pat.

4. The method of claim 1 wherein said modulating comprises sinusoidal modulating.

5. The method of claim 1 wherein said modulating comprises ramp modulating.

6. The method of claim 1 wherein said target depth is defined as a difference between an effective light path length of said reference light path and an effective light path length of said sensing light path.

7. The method of claim 1 wherein said reflecting device comprises a fixed reflecting device.

8. The method of claim 1 wherein at least one of said reference light path and said sensing light path comprises at least one of an optical fiber and a waveguide.

9. The method of claim 1 wherein said modulating said effective light path length is achieved with at least one of a modulator comprising metallic electrodes disposed at an optical waveguide and a modulator formed with an optical fiber wound on a piezoelectric drum forming at least a portion of at least one of said reference light path and said sensing light path.

10. The method of claim 1:
    wherein said modulating includes a phase parameter; and
    further comprising relating said change in said phase component to said phase parameter, wherein said phase parameter is indicative of said variation in said index of refraction.

11. The method of claim 10 wherein said phase parameter is indicative of said variation in said index of refraction as a ratio of said phase parameter to said target depth.

12. The method of claim 1 further including calibrating at least one of said reference light path and said sensing light path by adjusting effective light path length of at least one of said reference light path and said sensing light path based on a sample exhibiting properties including at least one of known refractive index and scattering coefficient.

13. The method of claim 1 wherein the characteristic of the analyte in the biological sample includes glucose concentration.

14. A system for determining a characteristic of an analyte in a biological sample, the system comprising:
a broadband light source for providing a broadband light;
a sensing light path receptive to said broadband light from said broadband light source, said sensing light path configured to direct said broadband light at the biological sample and to receive said broadband light reflected from the biological sample;
a reflecting device;
a reference light path receptive to said broadband light from said broadband light source, said reference light path configured to direct said broadband light at said reflecting device and to receive said broadband light reflected from said reflecting device, said reference light path and said sensing light path cooperating to define a target depth;
a modulator associated with at least one of said reference light path and said sensing light path, said modulator for modulating at about a distance of a center wavelength of said broadband light an effective light path length of said at least one of said reference light path and said sensing light path;
a detector receptive to said broadband light resulting from said broadband light reflected from the biological sample and said broadband light reflected from said reflecting device, said detector generating a signal indicative of an interference of said broadband light reflected from said target depth in the biological sample and said broadband light reflected from said reflecting device, wherein said signal is a product of a cosine function; and
processing means configured to determine a phase component that is an argument of the cosine function, said processing means further configured to determine a change in the phase component of said signal resulting from a change of said effective light path length that is itself induced by a change of a property of the biological sample, a variation in an index of refraction from said change in the phase component of said signal, and the characteristic of the analyte in the biological sample from said variation in said index of refraction.

15. The system of claim 14 further comprising
means for varying an effective light path length of at least one of said reference light path and said sensing light path to define an other target depth, said other target depth is at a distance of about at least a coherence length of said broadband light from, said target depth.

16. The system of claim 15 wherein said means for varying comprises a modulator comprising metallic electrodes disposed at an optical waveguide and a modulator formed with an optical fiber wound on a piezoelectric drum forming at least a portion of at least one of said reference light path and said sensing light path.

17. The system of claim 14 wherein said modulator comprises a sinusoidal modulator.

18. The system of claim 14 wherein said modulator comprises a ramp modulator.

19. The system of claim 14 wherein said effective light path length of said sensing light path is different from said effective light path length of said sensing light path by a difference, said target depth defined as said difference.

20. The system of claim 14 wherein said reflecting device comprises a fixed reflecting device.

21. The system of claim 14 wherein at least one of said reference light path and said sensing light path comprises at least one of an optical fiber and a waveguide.

22. The system of claim 14 wherein said modulator comprises at least one of metallic electrodes disposed at an optical waveguide and a plezoelectric drum with an optical fiber wound thereon forming at least a portion of at least one of said reference light path and said sensing light path.

23. The system of claim 14 wherein:
said modulator comprises modulating including a phase parameter; and
said processing means further configured to relate said change in said phase component to said phase parameter, wherein said phase parameter is indicative of said variation in said index of refraction.

24. The system of claim 14 further including a calibrating strip for calibrating at least one of said reference light path and said sensing light path by adjusting effective light path length of at least one of said reference light path and said sensing light path based on a sample exhibiting properties including at least one of known refractive index.

25. The system of claim 14 where in the characteristic of the analyte in the biological sample includes glucose concentration.

* * * * *